US007207991B2

(12) United States Patent
Michelson

(10) Patent No.: US 7,207,991 B2
(45) Date of Patent: Apr. 24, 2007

(54) METHOD FOR THE ENDOSCOPIC CORRECTION OF SPINAL DISEASE

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 674 days.

(21) Appl. No.: 10/100,701

(22) Filed: Mar. 18, 2002

(65) Prior Publication Data

US 2002/0091390 A1 Jul. 11, 2002

Related U.S. Application Data

(60) Continuation of application No. 08/480,461, filed on Jun. 7, 1995, which is a division of application No. 08/394,836, filed on Feb. 27, 1995, now Pat. No. 5,772,661, which is a continuation-in-part of application No. 08/219,626, filed on Mar. 28, 1994, which is a continuation-in-part of application No. 08/074,781, filed on Jun. 10, 1993, now Pat. No. 5,484,437, which is a continuation-in-part of application No. 07/698,674, filed on May 10, 1991, now abandoned, which is a division of application No. 07/205,935, filed on Jun. 13, 1988, now Pat. No. 5,015,247.

(51) Int. Cl.
*A61B 17/56* (2006.01)

(52) U.S. Cl. .................. 606/61; 623/16.11; 623/17.11; 623/17.16

(58) Field of Classification Search ............ 606/60–61, 606/72–79; 623/16.11, 17.11, 17.16
See application file for complete search history.

(56) References Cited

U.S. PATENT DOCUMENTS 350,420 A    10/1886    Dillon (Continued)

FOREIGN PATENT DOCUMENTS

DE    1961531    7/1970

(Continued)

OTHER PUBLICATIONS

Adams, et al.; Outline of Orthopaedics, Eleventh Edition; Trunk and Spine, p. 194.

(Continued)

*Primary Examiner*—Michael A. Brown
(74) *Attorney, Agent, or Firm*—Martin & Ferraro, LLP

(57) ABSTRACT

An improved method and instrumentation for performing spinal surgery, including discectomy, interbody fusion and rigid internal fixation of the spine, from the lateral aspect of the spine is disclosed. The surgical procedure can be performed through a very small incision. The instrumentation of the present invention, all of which is inserted from a lateral position into the spine in the preferred embodiment, comprises a guide pin, a distractor, an extended outer sleeve, an inner sleeve an adjustable drill and an implant driver. The distractor of the present invention is driven into the disc for spacing apart and realigning the adjacent vertebrae. It further functions as an alignment rod for inserting the extended outer sleeve which is a hollow tubular member capable of maintaining said spacing and alignment of two adjacent vertebrae and defines a protected space through which subsequent instruments which may include, but are not limited to, a drill and a diameter reducing inner sleeve may be passed, as well as a spinal implant. The remainder of the surgical procedure consisting of the removal of spinal material across the disc, fusion, and rigid internal stabilization via the implant may all be performed via the closed space within the extended outer sleeve.

49 Claims, 14 Drawing Sheets

U.S. PATENT DOCUMENTS

| | | |
|---|---|---|
| 1,137,585 A | 4/1915 | Craig |
| 2,065,659 A | 12/1936 | Cullen |
| 2,181,746 A | 11/1939 | Siebrandt |
| 2,243,718 A | 5/1941 | Moreira |
| 2,372,622 A | 3/1945 | Fassio |
| 2,514,665 A | 7/1950 | Mylier |
| 2,537,070 A | 1/1951 | Longfellow |
| 2,543,780 A | 3/1951 | Hipps et al. |
| 2,677,369 A | 5/1954 | Knowles |
| 2,774,350 A | 12/1956 | Cleveland |
| 2,789,558 A | 4/1957 | Rush |
| 2,832,343 A | 4/1958 | Mose |
| 2,842,131 A | 7/1958 | Smith |
| 2,878,809 A | 3/1959 | Treace |
| 3,128,768 A | 4/1964 | Geistauts |
| 3,298,372 A | 1/1967 | Feinberg |
| 3,426,364 A | 2/1969 | Lumb |
| 3,486,505 A | 12/1969 | Morrison |
| 3,604,487 A | 9/1971 | Gilbert |
| 3,605,123 A | 9/1971 | Hahn |
| 3,618,611 A | 11/1971 | Urban |
| 3,709,219 A | 1/1973 | Halloran |
| 3,719,186 A | 3/1973 | Merig, Jr. |
| 3,720,959 A | 3/1973 | Hahn |
| 3,750,652 A | 8/1973 | Sherwin |
| 3,848,601 A | 11/1974 | Ma et al. |
| 3,855,638 A | 12/1974 | Pilliar |
| 3,867,728 A | 2/1975 | Stubstad et al. |
| 3,867,950 A | 2/1975 | Fischell |
| 3,875,595 A | 4/1975 | Froning |
| 3,888,260 A | 6/1975 | Fischell |
| 3,892,232 A | 7/1975 | Neufeld |
| 3,905,047 A | 9/1975 | Long |
| 3,915,151 A | 10/1975 | Kraus |
| 3,916,907 A | 11/1975 | Peterson |
| 3,918,440 A | 11/1975 | Kraus |
| 3,941,127 A | 3/1976 | Froning |
| 3,942,535 A | 3/1976 | Schulman |
| 3,948,262 A | 4/1976 | Zaffaroni |
| 3,952,334 A | 4/1976 | Bokros et al. |
| 3,987,499 A | 10/1976 | Scharbach et al. |
| 4,016,651 A | 4/1977 | Kawahara et al. |
| 4,027,392 A | 6/1977 | Sawyer et al. |
| D245,259 S | 8/1977 | Shen |
| 4,051,905 A | 10/1977 | Kleine |
| 4,059,115 A | 11/1977 | Jumashev et al. |
| 4,070,514 A | 1/1978 | Eatherly et al. |
| 4,082,097 A | 4/1978 | Mann et al. |
| 4,086,701 A | 5/1978 | Kawahara et al. |
| 4,124,026 A | 11/1978 | Berner et al. |
| 4,142,517 A | 3/1979 | Stavropoulos et al. |
| 4,168,326 A | 9/1979 | Broemer et al. |
| 4,175,555 A | 11/1979 | Herbert |
| 4,177,524 A | 12/1979 | Grell et al. |
| 4,181,457 A | 1/1980 | Holmes |
| 4,197,850 A | 4/1980 | Schulman et al. |
| 4,206,516 A | 6/1980 | Pilliar |
| 4,222,128 A | 9/1980 | Tomonaga et al. |
| D257,511 S | 11/1980 | Zahn |
| 4,232,679 A | 11/1980 | Schulman |
| 4,237,948 A | 12/1980 | Jones et al. |
| 4,258,716 A | 3/1981 | Sutherland |
| 4,259,072 A | 3/1981 | Hirabayashi et al. |
| 4,262,369 A | 4/1981 | Roux |
| 4,271,832 A | 6/1981 | Evans et al. |
| D260,525 S | 9/1981 | Lassiter |
| 4,289,123 A | 9/1981 | Dunn |
| 4,293,962 A | 10/1981 | Fuson |
| 4,309,777 A | 1/1982 | Patil |
| 4,328,593 A | 5/1982 | Sutter et al. |
| 4,333,469 A | 6/1982 | Jeffcoat et al. |
| 4,341,206 A | 7/1982 | Perrett et al. |
| 4,349,921 A | 9/1982 | Kuntz |
| 4,356,572 A | 11/1982 | Guillemin et al. |
| 4,401,112 A | 8/1983 | Rezaian |
| 4,405,319 A | 9/1983 | Cosentino |
| 4,414,979 A | 11/1983 | Hirshorn et al. |
| 4,423,721 A | 1/1984 | Otte et al. |
| 4,439,152 A | 3/1984 | Small |
| 4,450,834 A | 5/1984 | Fischer |
| 4,484,570 A | 11/1984 | Sutter et al. |
| 4,492,226 A | 1/1985 | Belykh et al. |
| 4,497,320 A | 2/1985 | Nicholson et al. |
| 4,501,269 A | 2/1985 | Bagby |
| 4,507,115 A | 3/1985 | Kambara et al. |
| RE31,865 E | 4/1985 | Roux |
| 4,530,360 A | 7/1985 | Duarte |
| 4,535,374 A | 8/1985 | Anderson et al. |
| 4,535,485 A | 8/1985 | Ashman et al. |
| 4,542,539 A | 9/1985 | Rowe, Jr. et al. |
| 4,545,374 A | 10/1985 | Jacobson |
| 4,547,390 A | 10/1985 | Ashman et al. |
| 4,549,547 A | 10/1985 | Brighton et al. |
| 4,552,200 A | 11/1985 | Sinha et al. |
| 4,553,273 A | 11/1985 | Wu |
| 4,554,914 A | 11/1985 | Kapp et al. |
| D281,814 S | 12/1985 | Pratt et al. |
| 4,570,623 A | 2/1986 | Ellison et al. |
| 4,570,624 A | 2/1986 | Wu |
| 4,573,448 A | 3/1986 | Kambin |
| 4,592,346 A | 6/1986 | Jurgutis |
| 4,599,086 A | 7/1986 | Doty |
| 4,600,000 A | 7/1986 | Edwards |
| 4,602,638 A | 7/1986 | Adams |
| 4,604,995 A | 8/1986 | Stephens et al. |
| 4,608,052 A | 8/1986 | Van Kampen et al. |
| 4,611,581 A | 9/1986 | Steffee |
| 4,619,264 A | 10/1986 | Singh |
| 4,628,921 A | 12/1986 | Rousso |
| 4,634,720 A | 1/1987 | Dorman et al. |
| 4,636,217 A | 1/1987 | Ogilvie et al. |
| 4,636,526 A | 1/1987 | Dorman et al. |
| 4,645,503 A | 2/1987 | Lin et al. |
| 4,653,486 A | 3/1987 | Coker |
| 4,653,509 A | 3/1987 | Oloff et al. |
| 4,655,777 A | 4/1987 | Dunn et al. |
| 4,661,536 A | 4/1987 | Dorman et al. |
| 4,664,567 A | 5/1987 | Edwards |
| 4,665,920 A | 5/1987 | Campbell |
| 4,677,883 A | 7/1987 | Lee |
| 4,677,972 A | 7/1987 | Tornier |
| 4,693,721 A | 9/1987 | Ducheyne |
| 4,696,290 A | 9/1987 | Steffee |
| 4,698,375 A | 10/1987 | Dorman et al. |
| 4,710,075 A | 12/1987 | Davison |
| 4,713,004 A | 12/1987 | Linkow et al. |
| 4,714,469 A | 12/1987 | Kenna |
| 4,721,103 A | 1/1988 | Freedland |
| 4,736,738 A | 4/1988 | Lipovsek et al. |
| 4,232,679 A | 5/1988 | Schulman |
| 4,743,256 A | 5/1988 | Brantigan |
| 4,743,260 A | 5/1988 | Burton |
| 4,759,766 A | 7/1988 | Buettner-Janz et al. |
| 4,759,769 A | 7/1988 | Hedman et al. |
| 4,769,881 A | 9/1988 | Pedigo et al. |
| 4,772,286 A | 9/1988 | Goble et al. |
| 4,781,591 A | 11/1988 | Allen |
| 4,790,303 A | 12/1988 | Steffee |
| 4,805,602 A | 2/1989 | Puno et al. |
| 4,820,305 A | 4/1989 | Harms et al. |
| 4,830,000 A | 5/1989 | Shutt |
| 4,834,757 A | 5/1989 | Brantigan |
| 4,848,327 A | 7/1989 | Perdue |
| 4,851,008 A | 7/1989 | Johnson |

| | | |
|---|---|---|
| 4,863,476 A | 9/1989 | Shepperd |
| 4,863,477 A | 9/1989 | Monson |
| 4,865,603 A | 9/1989 | Noiles |
| 4,877,020 A | 10/1989 | Vich |
| 4,878,915 A | 11/1989 | Brantigan |
| 4,903,882 A | 2/1990 | Long |
| 4,904,260 A | 2/1990 | Ray et al. |
| 4,904,261 A | 2/1990 | Dove et al. |
| 4,911,718 A | 3/1990 | Lee et al. |
| 4,913,144 A | 4/1990 | Del Medico |
| 4,936,848 A | 6/1990 | Bagby |
| 4,943,291 A | 7/1990 | Tanguy |
| 4,955,885 A | 9/1990 | Meyers |
| 4,955,908 A | 9/1990 | Frey et al. |
| 4,957,495 A | 9/1990 | Kluger |
| 4,960,420 A | 10/1990 | Goble et al. |
| 4,961,740 A | 10/1990 | Ray et al. |
| 4,968,316 A | 11/1990 | Hergenroeder |
| 4,969,888 A | 11/1990 | Scholten et al. |
| 4,987,904 A | 1/1991 | Wilson |
| 5,015,247 A | 5/1991 | Michelson |
| 5,015,255 A | 5/1991 | Kuslich |
| 5,026,373 A | 6/1991 | Ray et al. |
| 5,030,236 A | 7/1991 | Dean |
| 5,047,036 A | 9/1991 | Koutrouvelis |
| 5,055,104 A | 10/1991 | Ray |
| 5,059,193 A | 10/1991 | Kuslich |
| 5,062,845 A | 11/1991 | Kuslich et al. |
| 5,071,437 A | 12/1991 | Steffee |
| 5,084,050 A | 1/1992 | Draenert |
| 5,102,414 A | 4/1992 | Kirsch |
| 5,105,819 A | 4/1992 | Wollschlager et al. |
| 5,108,422 A | 4/1992 | Green et al. |
| 5,112,336 A | 5/1992 | Krevolin et al. |
| 5,116,304 A | 5/1992 | Cadwell |
| 5,122,130 A | 6/1992 | Keller |
| 5,123,926 A | 6/1992 | Pisharodi |
| 5,171,278 A | 12/1992 | Pisharodi |
| 5,171,279 A | 12/1992 | Mathews |
| 5,183,471 A | 2/1993 | Wilk |
| 5,192,327 A | 3/1993 | Brantigan |
| 5,242,443 A | 9/1993 | Kambin |
| 5,246,458 A | 9/1993 | Graham |
| 5,258,031 A | 11/1993 | Salib et al. |
| 5,263,953 A | 11/1993 | Bagby |
| 5,269,772 A | 12/1993 | Wilk |
| 5,279,292 A | 1/1994 | Baumann et al. |
| 5,292,252 A | 3/1994 | Nickerson et al. |
| 5,306,309 A | 4/1994 | Wagner et al. |
| 5,314,427 A | 5/1994 | Goble et al. |
| 5,314,432 A | 5/1994 | Paul |
| 5,324,295 A | 6/1994 | Shapiro |
| 5,352,229 A | 10/1994 | Goble et al. |
| 5,360,430 A | 11/1994 | Lin |
| 5,364,399 A | 11/1994 | Lowery et al. |
| 5,370,662 A | 12/1994 | Stone et al. |
| 5,370,697 A | 12/1994 | Baumgartner |
| 5,393,036 A | 2/1995 | Sheridan |
| RE34,871 E | 3/1995 | McGuire et al. |
| 5,395,317 A | 3/1995 | Kambin |
| 5,395,372 A | 3/1995 | Holt et al. |
| 5,396,880 A | 3/1995 | Kagan et al. |
| 5,397,364 A | 3/1995 | Kozak et al. |
| 5,425,772 A | 6/1995 | Brantigan |
| 5,435,723 A | 7/1995 | O'Brien |
| 5,441,527 A | 8/1995 | Erickson et al. |
| 5,443,514 A | 8/1995 | Steffee |
| 5,458,638 A | 10/1995 | Kuslich et al. |
| 5,489,307 A | 2/1996 | Kuslich et al. |
| 5,489,308 A | 2/1996 | Kuslich et al. |
| D368,777 S | 4/1996 | Goble et al. |
| 5,571,109 A | 11/1996 | Bertagnoli |
| 4,971,740 A | 1/1997 | Nishio et al. |
| 5,658,337 A | 8/1997 | Kohrs et al. |
| 5,683,463 A | 11/1997 | Godefroy et al. |
| 5,766,252 A | 6/1998 | Henry et al. |
| D397,439 S | 8/1998 | Koros et al. |
| 5,800,547 A | 9/1998 | Schafer et al. |

FOREIGN PATENT DOCUMENTS

| | | |
|---|---|---|
| DE | 24 46 039 | 4/1975 |
| DE | 3101333 A1 | 12/1981 |
| DE | 3132520 A1 | 6/1982 |
| DE | 3505567 A1 | 6/1986 |
| DE | 36 08 163 A1 | 9/1987 |
| DE | 41 04 359 A1 | 8/1992 |
| EP | 0 077 159 | 4/1983 |
| EP | 0 162 005 | 11/1985 |
| EP | 0 179 695 | 4/1986 |
| EP | 0 260 044 | 3/1988 |
| EP | 0303241 A2 | 2/1989 |
| EP | 0 307 241 B1 | 3/1989 |
| EP | 0499465 A1 | 8/1992 |
| EP | 0551187 A1 | 7/1993 |
| EP | 0577179 A1 | 1/1994 |
| EP | 0599419 A2 | 6/1994 |
| EP | 0627204 A2 | 12/1994 |
| EP | 0637440 B1 | 10/1997 |
| ES | 283078 | 5/1985 |
| FR | 2 295 729 | 7/1976 |
| FR | 2 581 336 | 11/1986 |
| FR | 2 703 580 | 10/1994 |
| GB | 1291470 | 10/1972 |
| GB | 1492990 | 11/1977 |
| GB | 1531487 | 11/1978 |
| GB | 2076657 A | 12/1981 |
| GB | 2082754 A | 3/1982 |
| GB | 2126094 A | 3/1984 |
| GB | 2164277 A | 3/1986 |
| JP | 57-29348 | 2/1982 |
| JP | 60-31706 | 2/1985 |
| JP | 60-43984 | 3/1985 |
| JP | 61-122859 | 6/1986 |
| JP | 62-155846 | 7/1987 |
| SE | 106 101 | 7/1939 |
| SU | 1107854 | 8/1984 |
| SU | 1124960 | 11/1984 |
| SU | 1217374 | 3/1986 |
| SU | 1222254 | 4/1986 |
| WO | 84/01298 | 4/1984 |
| WO | 91/06266 | 5/1991 |
| WO | 92/14423 | 9/1992 |
| WO | 93/01771 | 2/1993 |
| WO | WO 94/28824 | 12/1994 |
| WO | 95/08964 | 4/1995 |
| WO | 96/22747 | 8/1996 |

OTHER PUBLICATIONS

Herkowitz, et al.; Principles of Bone Fusion; The Spine, Third Edition; Chapter 44, p. 1739.

Muschler, et al.; The Biology of Spinal Fusion; Spinal Fusion Science and Technique, Cotler and Cotler, pp. 9-13.

Zindrick, et al.; Lumbar Spine Fusion: Different Types and Indications; The Lumbar Spine, vol. 1, Second Edition, pp. 588-593 (1996).

Gillingham, F.J., et al.; Automatic Patient Monitoring in the Ward; Brit. J. Surg., vol. 53, No. 10, pp. 864-866 (Oct. 1966).

Maloney, A.F.J., et al.; Clinical and Pathological Observations in Fatal Head Injuries, Brit. J. Surg., vol. 56, No. 1, pp. 23-31 (Jan. 1969).

Harris, P., et al.; Spinal Deformity After Spinal Cord Injury; Paraplegia, vol. 6, No. 4, pp. 232-238 (Feb. 1969).

Gillingham, F.J., et al.; Head injuries; Proceedings of the 18th World Congress of the International College of Surgeons, Rome, pp. 68-71 (May 28-31, 1972).

Whatmore, W. J.; Sincipital Encephalomenigoceles; Brit. J. Surg., vol. 60, No. 4, pp. 261-270 (Apr. 1973).

Whatmore, W. J.; Meningioma Following Trauma; Brit. J. Surg., vol. 60, No. 6, pp. 496-498 (Jun. 1973).

Bagby, George W.; Wobbler Syndrome in Horses (the Ataxic Horse); Spokane County Medical Society Bulletin; Spring 1979.

Rathke, F.W., et al.; Surgery of the Spine; Atlas of Orthopaedic Operations, vol. 1, p. 137, W.B. Saunders Co., Philadelphia (1979).

Albrektsson, T., et al.; Osseointegrated Titanium Implants; Acta. Orthop. Scand.; vol. 52:155-170 (1981).

Raveh, J., et al.; Neue Rekonstruktionsmoglichkeiten des Unterkiefers bei knochemen Defekten nach Tumorresektionen; Der Chirurg vol. 53:459-467 (1982).

Crock, H. V.; Practice of Spinal Surgery; Springer-Verlag/Wien, New York (1983).

DeBowes, R.M., et al.; Study of Bovine . . . Steel Baskets; Transactions of the 29th Annual Meeting; Orthopaedic Research Society, vol. 8, p. 407, Mar. 8-10 (1983).

O'Neill, P., et al.; Spinal Meningoceles in Association with Neurofibromatosis; Neurosurgery, vol. 13, No. 1, pp. 82-84 (Jul. 1983).

Brandt, L., et al.; A Dowel Inserter for Anterior Cervical Interbody Fusion; J. Neurosurg. 61:793-794 (Oct. 1984).

Whatmore, W.J., et al.; The Coventry Cervical Spreader and Dowel Inserter; ACTA Neurochirurgica, vol. 70, FASC. 1-2 (1984).

Raveh, J., et al.; Use of the Titanium-coated Hollow Screw and Reconstruction Plate System in Bridging of Lower Jaw Defects; J. Oral Maxillofac Surg. 42:281-294 (1984).

Otero-Vich, Jose M.; Anterior Cervical Interbody Fusion with Threaded Cylindrical Bone; J. Neurosurg 63:750-753 (Nov. 1985).

Morscher, E., et al.; Die vordere Verplattung der Halswirbelsäule mit dem Hohlschrauben-Plattensystem aus Titanium, *Der Chirurg*, vol. 57, pp. 702-707 (1986) with English Translation.

Bagby, G.W.; Basket Implant Facilitates Spinal Fusion; Orthopedics Today, vol. 7, No. 10, (Oct. 1987).

Butts, M. K., et al.; Biomechanical Analysis of a New Method for Spinal Interbody Fixation; 1987 Symposium, American Society of Mechanical Engineers, "Advances in Bioengineering", Boston, MA (Dec. 13-18, 1987).

Crawley et al.; A Modified Cloward's Technique for Arthrodesis of the Normal Metacarpophalangeal Joint in the Horse; Veterinary Surgery, vol. 17, No. 3, pp. 117-127 (1988).

Raveh, J., et al.; Surgical Procedures for Reconstruction of the Lower Jaw Using the Titanium-Coated Hollow-Screw Reconstruction Plate System: Bridging of Defects; Otolaryngologic Clinics of North America; vol. 20, No. 3 pp. 535-558 (Aug. 1987).

Whatmore, W. J.; Proceedings of the Society of British Neurological Surgeons; Journal of Neurology, Neurosurgery, and Psychiatry, 50:1093-1100 (1987).

Goldthwaite, N., et al.; Toward Percutaneous Spine Fusion; Ch. 45; Lumbar Spine Surgery; C.V. Mosby Company, pp. 512-522 (1987).

Bagby, G.W.; Arthrodesis by the Distraction-Compression Method Using a Stainless Steel Implant; Orthopedics, vol. II, No. 6, pp. 931-934 (Jun. 1987).

Itoman, M., et al.; Banked Bone Grafting for Bone Defect Repair—Clinical Evaluation of Bone Union and Graft Incorporation; J. Jpn. Orthop. Assoc. 62:461-469 (1988).

Kane, W.J.; Direct Current Electrical Bone Growth Stimulation for Spinal Fusion; Spine, vol. 13, No. 3, pp. 363-365 (Mar. 1988).

The SpF-T Spinal Fusion Stimulator: An Efficacious Adjunct that Meets the Diverse Needs of Spine Patients; EBI Medical Systems; (Aug. 1991).

Schmitz et al.; Performance of Alloplastic Materials and Design of an Artificial Disc; The Artificial Disc, Brock, Mayer, Weigel; pp. 23-34 (1991).

The Use of Direct Current for Electrically Induced Osteogenesis; The Positive Effect of an Electronegative charge on Bone Growth; EBI Medical Systems (Feb. 1993).

Mylonas, C., et al.; Anterior Cervical Decompression and Fusion Using the Coventry Cervical Spreader and Dowel Inserter; British Journal of Neurosurgery, 7:545-549 (1993).

Fusion of the Lumbar Spine; Anterior Monosegmental Fusion L5-S1, Atlas of Spinal Operations, Thieme, pp. 270-274 (1993).

Spine Basics, Danek Group, Inc., Glossary (1993).

Lumbar Spine Surgery, Techniques & Complications; History of Lumbar Spine Surgery (1994) pp. 11-15; 27; 30; 35-45; 265-268.

FIG. 18
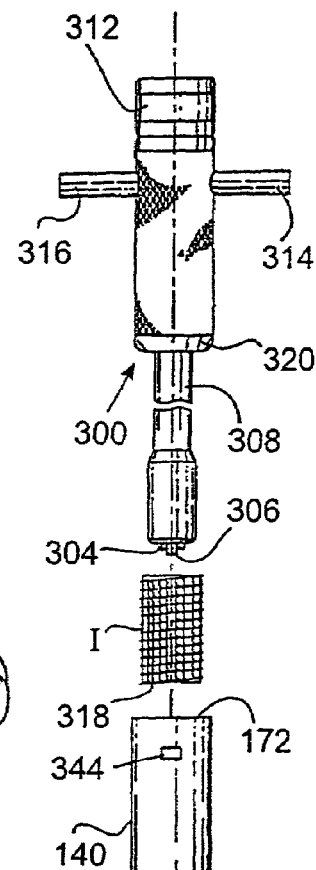
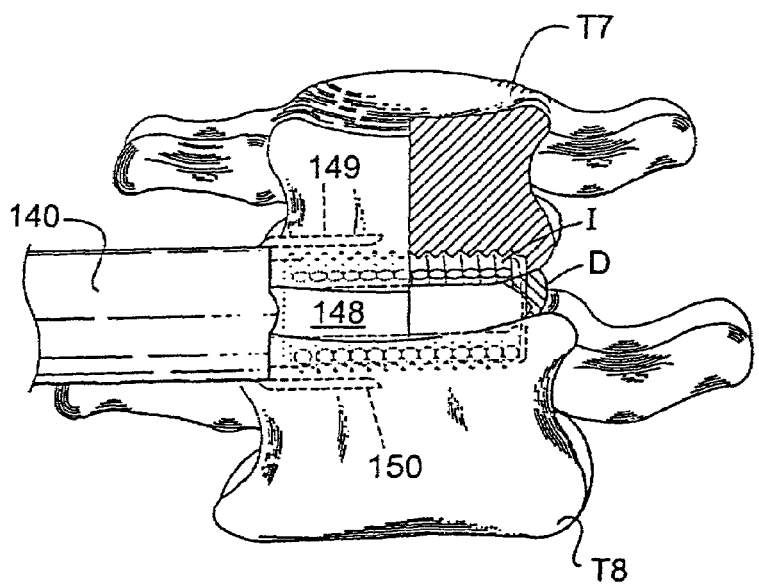
FIG. 19
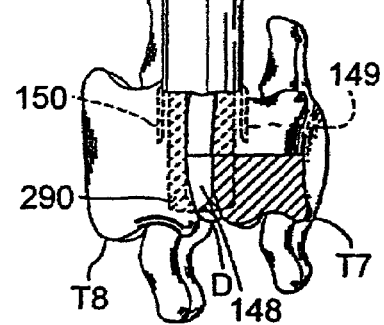

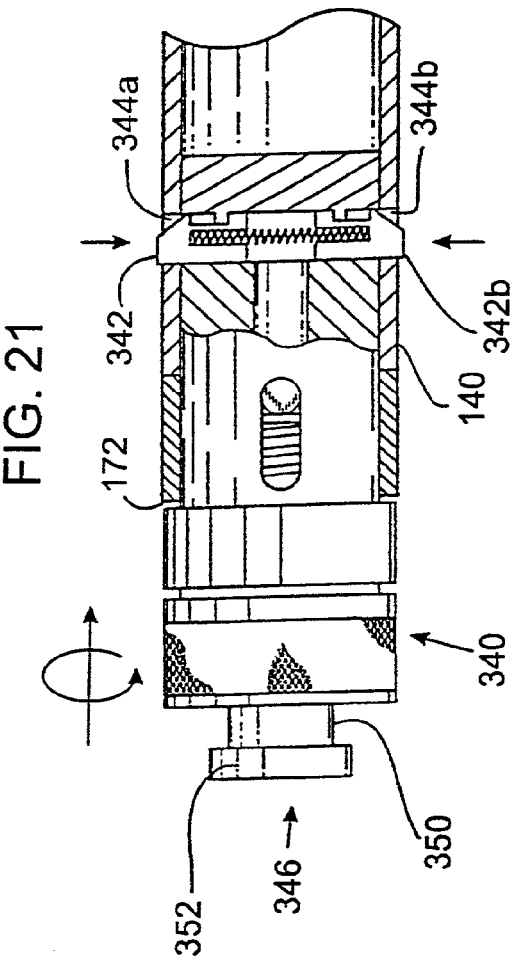
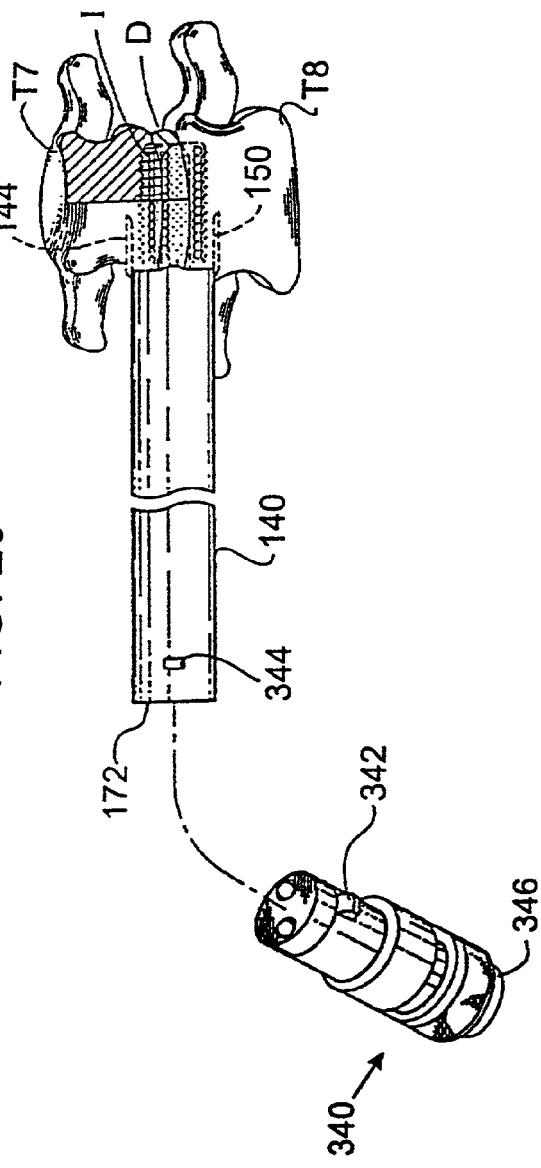

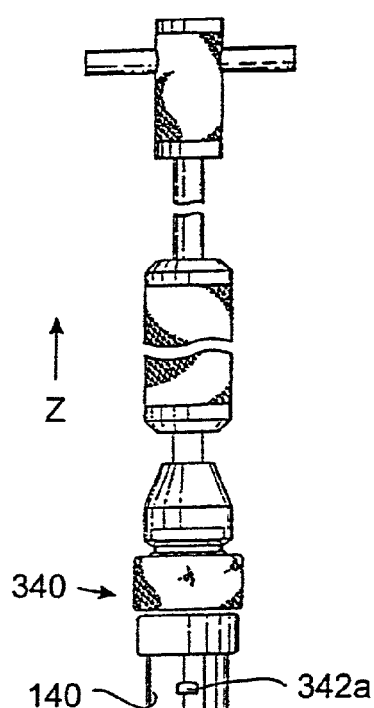
FIG. 22
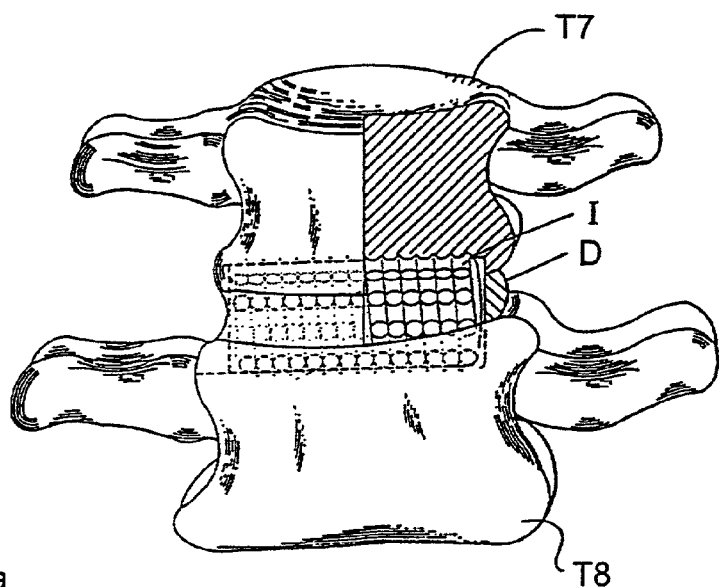
FIG. 23
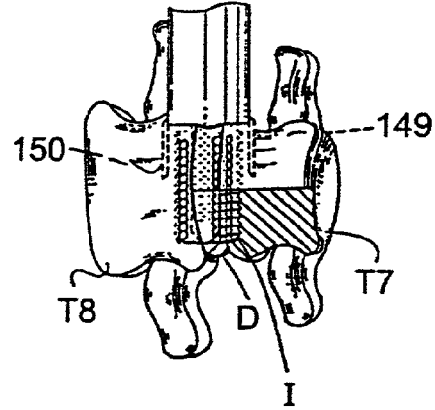
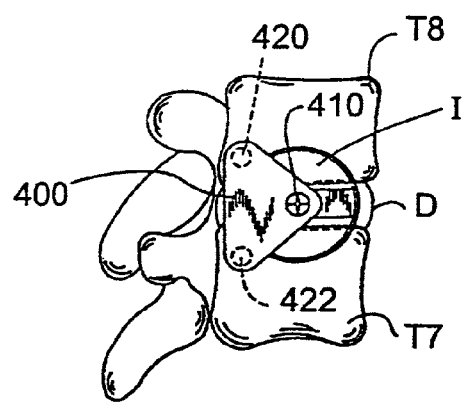
FIG. 24

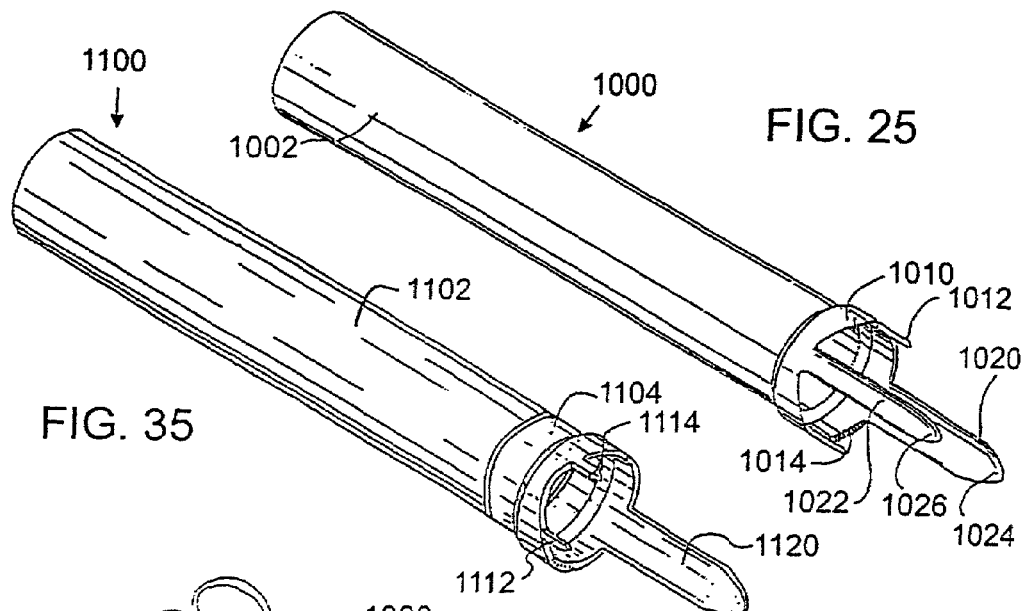
FIG. 25
FIG. 35
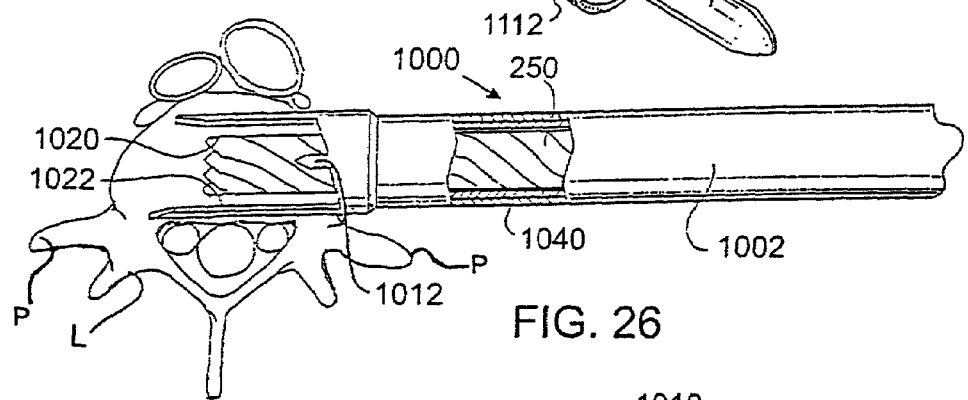
FIG. 26
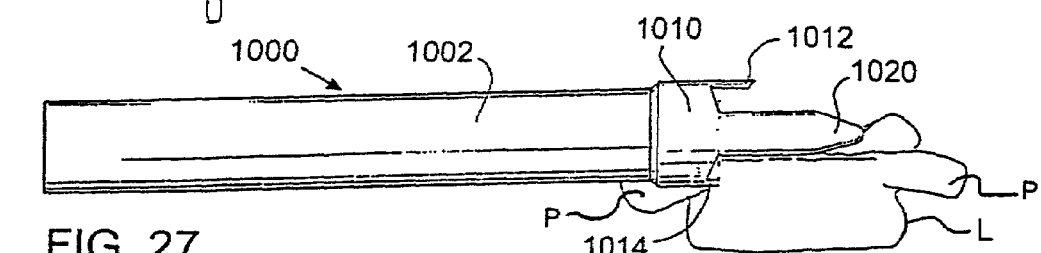
FIG. 27
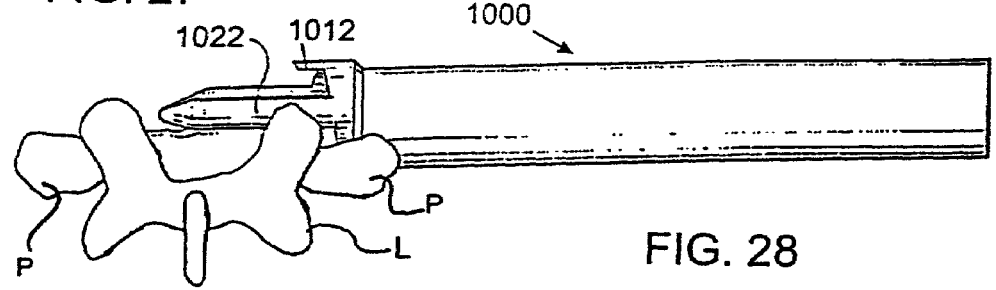
FIG. 28

METHOD FOR THE ENDOSCOPIC CORRECTION OF SPINAL DISEASE

RELATED APPLICATIONS

This is a continuation of application Ser. No. 08/480,461, filed Jun. 7, 1995; which is a division of application Ser. No. 08/394,836, filed Feb. 27, 1995 now U.S. Pat. No. 5,772,661; all of which are incorporated herein by reference, which is a continuation in part of U.S. application Ser. No. 08/074,781 filed on Jun. 10, 1993 now U.S. Pat. No. 5,484,437, which is a continuation in part of U.S. application Ser. No. 07/698,674 filed on May 10, 1991 now abandoned which is a divisional of application Ser. No. 07/205,935 filed on Jun. 13, 1988, now U.S. Pat. No. 5,015,247 all of which are incorporated herein by reference. This application is also a continuation in part of U.S. application Ser. No. 08/219,626 filed on Mar. 28, 1994 which is incorporated herein by reference.

FIELD OF THE INVENTION

The present invention relates generally to instrumentation and methods of performing surgical procedures on the human thoracic and lumbar spine along the lateral aspect of the spine and from a true lateral or anterolateral approach, and specifically to the surgical correction of thoracic and lumbar disc disease and spinal deformities where concomitant fusion is desired.

DESCRIPTION OF THE RELATED ART

As regards the thoracic spine, it may be afflicted with a variety of ailments, some so severe as to require surgical intervention. A disc herniation may compress the spinal cord and/or nerve roots and cause pain, loss of function, and even complete paralysis of the legs with loss of bowel and bladder control. The correct treatment for such conditions is the removal of the offending discal tissue. However, this has proven both difficult and quite dangerous. When the discs of the thoracic spine are approached posteriorly (from behind) the spinal cord is in the way. To approach the same herniation anteriorly (from the front) requires the very formidable procedure of thoracotomy (cutting open the chest) and moving the heart and lungs out of the way. procedures from a lateral approach to the spine (from the side) using fiber optic viewing instruments called thorascopes and numerous small surgical openings through the chest wall (portals) through which various surgical instruments, such as burrs, rongeurs and curettes, may be placed to remove these disc herniations while avoiding formal thoracotomy. Because the discs are very narrow in the thoracic spine and the surgeon is approaching the spine laterally, there is very little space in which to work as the disc is entered in order to get to the back of the disc space. Therefore, the amount of disc removal may be limited. In the alternative, the surgeon might remove the pedicle to gain access to the spinal canal risking further weakening of the already diseased area.

Sometimes, for a variety of reasons including the removal of disc material, the thoracic spine may become unstable (too much motion) at any given level. Historically, this has been treated by fusion, the joining together permanently of the unstable vertebrae via a bridge of bone so as to eliminate all motion at that location. Fusions about the thoracic spine have been performed either anteriorly or posteriorly, either procedure being a rather large surgical undertaking.

Stability of the spine is required for fusion to occur. For this reason, and for the purpose of correcting spinal deformity, it is often necessary to use hardware to rigidly internally fixate (stabilize) the spine. To date, the only benefit the use of the thorascope has provided in this regard is to allow the previous thoracotomy incision to be somewhat smaller.

So to date the following problems remain even utilizing the most recent technology as regards the surgical treatment of thoracic disc disease:

Firstly, the working space within the disc itself to access the herniation which is more posterior is quite limited.

Secondly, multiple or long incisions through the chest are still required.

Thirdly, when fusion is required a major surgical undertaking with its considerable risks is required.

Fourthly, the installation of hardware affixed to the spine still requires a thoracotomy, albeit a smaller one if visualization is assisted via the thorascope.

Fifthly, when, as is often the case, the patient requires all three, that is, discectomy (excision, in part or whole, of an intervertebral disc), fusion, and the application of hardware to the spine, those procedures are performed as serially (one after the other) combined surgical procedures with added surgical times, complications, morbidities, and mortalities.

As regards to the human lumbar spine, the treatment of discal disease with neural compression has generally been from a posterior (from behind) approach. This is sensible as the lumbar discs are generally quite large and it is only those protrusions occurring posteriorly which compress the neural elements which are themselves posterior to the discs. These posterior approaches have included both true posterior approaches and posterolateral approaches to the discs. Further, such approaches have been made via open incisions or through percutaneous stab wounds. In the latter case, instruments are inserted through the stab wounds and monitored by the use of radiographic imaging or the use of an endoscopic viewing device. While it is possible to also decompress a posterior disc herniation in the lumbar spine from an anterior approach (from the front) doing so requires the removal of a very substantial portion or all of the disc material in the front and mid portions of the disc thus leaving that disc incompetent and that spinal segment generally unstable. Therefore, such an anterior approach to the lumbar spine has been reserved for those instances where a fusion is to be performed in conjunction with, and following such a disc removal.

As regards to fusion, the application of bone or bone like substances between bones to induce bony bridging, such procedures have been performed outside the vertebral bodies and/or between the vertebral bodies. The latter being known as an interbody fusion. Such interbody fusions have been performed from posterior, posterolateral and anterior. The adjective applying specifically to the direction from which the bone grafts enter the intervertebral space. Interbody fusion from the posterior approach while still in use has been associated with significant complications generally related to the fact that the delicate dural sac and the spine nerves cover the back of the disc space and are thus clearly in harms way with such an approach. The posterolateral approach has generally been utilized as a compliment to percutaneous discectomy and has consisted of pushing tiny fragments of morsalized bone down through a tube and into the disc space.

Anterior interbody spinal fusion is performed from a straight anterior position as regards the path of entry of the fusion material into the intervertebral space. Such an anterior position is achieved in one of two ways. First, by a straight anterior approach which requires that the peritoneal cavity, which contains the intestines and other organs, be punctured twice, once through the front and once through the back on the way to the front of the spine; or secondly, by starting on the front of the abdomen off to one side and dissecting behind the peritoneal cavity on the way to the front of the spine. Regardless of which approach to the front of the spine is used, and apart from the obvious dangers related to the dense anatomy and vital structures in that area, there are at least two major problems specific to the anterior interbody fusion angle of implant insertion itself. First, generally at the $L_4L_5$ disc, the great iliac vessels bifurcate from the inferior vena cava lie in close apposition to, and, covering that disc space making fusion from the front both difficult and dangerous. Secondly, anterior fusions have generally been done by filling the disc space with bone or by drilling across the disc space and then filling those holes with cylindrical implants. As presently practiced, the preferred method of filling the disc space consists of placing a ring of allograft (bone not from the patient) femur into that disc space. An attempt to get good fill of the disc space places the sympathetic nerves along the sides of the disc at great risk. Alternatively, when the dowel technique is used, because of the short path from the front of the vertebrae to the back and because of the height of the disc as compared to the width of the spine, only a portion of the cylindrical implant or implants actually engages the vertebrae, thus, compromising the support provided to the vertebrae and the area of contact provided for the fusion to occur.

There is therefore, in regard to the lumbar spine, a need for a new method and means for achieving interbody fusion which method avoids the problems associated with all prior methods, and which have included, but are not limited to, nerve damage when performed posteriorly, or the need to mobilize the great vessels when performed anteriorly. Further, the size of the implants are limited by the dural sac posteriorly, and the width of the spine and the delicate vital structures therewith associated anteriorly. An improved method and means for interbody fusion should provide for optimal fill of the interspace without endangering the associated structures and allow for the optimal area of contact between the implant or implants and the vertebrae to be fused.

SUMMARY OF THE INVENTION

The present invention is directed to methods and instrumentation for performing surgery on the spine along its lateral aspect (side) and generally by a lateral or an anterolateral surgical approach, such that the instruments enter the body from an approach that is other than posterior and make contact with the spine along its lateral aspect. The present invention provides for the entire surgical procedure to be performed through a relatively small incision and may be performed in either the thoracic or lumbar spine.

In the preferred embodiment, the instrumentation of the present invention comprises a guide pin, a distractor, an extended outer sleeve, an inner sleeve and drill adjustable for depth and with a depth limiting means. The distractor of the present invention is used for initially distracting (spacing apart) and realigning adjacent vertebrae of the spine and also functions as an alignment rod for inserting the extended outer sleeve. The distractor is placed at the affected disc space between adjacent vertebrae through a small incision in the body. For example, for surgery in the thoracic spine, a small incision in the chest cavity of the patient is made from a lateral approach to the thoracic spine. For surgery in the lumbar spine a small incision may be made in the abdominal wall of the patient. The insertion of the distractor may be guided by a guide pin previously inserted in the disc space and visually monitored for proper orientation and placement by the surgeon either indirectly through an image intensifier, or directly through a thorascope or by direct vision.

The extended outer sleeve in the preferred embodiment is a hollow tubular member having an extension member that is inserted in the disc space and is capable of distracting and aligning the two adjacent vertebrae from the lateral aspect of the spine. In the preferred embodiment, the extended outer sleeve has a pair of prongs for fixedly engaging the two adjacent vertebrae and further stabilizing the adjacent vertebrae. With the distractor in place in the affected disc space, the extended outer sleeve is placed over the distractor, and the distractor guides and aligns the insertion of the extended outer sleeve. As the extended outer sleeve is seated, the extension member becomes inserted in the disc space and the prongs engage the outside wall of the adjacent vertebrae. The distractor is then removed and the extended outer sleeve maintains the proper distraction and alignment of the adjacent vertebrae. The remainder of the surgical procedure consisting of disc removal, fusion, and rigid internal stabilization may all be performed via the closed space within the extended outer sleeve. Alternatively, a convertible extended outer sleeve comprising a hollow tubular member that can be dissociated from its insertion end which remains engaged to the vertebrae to maintain distraction and alignment, may be used where it is desired to have direct visualization and access to the surgical site for at least a portion of the surgical procedure.

The drilling out and the subsequent removal of a rather significant mass of the disc itself may be curative in relieving a posterior disc herniation as the mass of tissue pushing from within the disc outward and posteriorly is thus removed. Further, the distractor in driving the vertebrae apart exerts significant tension on the walls of the disc which are pulled straight also tending to correct any disc herniation. Finally, since the hole drilled across the disc space is quite close to the posterior borders of the vertebrae, it makes the removal of any persisting posterior disc herniation quite simple. With the drill removed and the extended outer sleeve cleaned out by irrigation and suction, one can then place the endoscope directly down the outer sleeve and into the large space created by the removal of the disc, and in the preferred method, the adjacent vertebral bone, and then remove any remaining fragments of disc using conventional hand held instruments such as rongeurs and curettes under endoscopic visualization.

When it is desirable to remove posterior disc material, then a specialized modification of the extended outer sleeve having at its distal end a spine engaging portion comprising one anterior extension and posteriorly two prongs one each above and below the disc space may be used. Further, such an extended outer sleeve may be configured such that the great length of the hollow tubular portion of the extended outer sleeve is detachable, as by unscrewing, from the distal working end such that when uncoupled the distal end may remain in place maintaining distraction even after the hole is drilled and thus allowing the surgeon to work through that remaining portion of the extended outer sleeve and the space provided by the drilling to remove the posterior disc material under direct vision. For those instances where the surgeon has elected to access the spine through a more standard incision and is viewing the spine directly, the surgeon is then able to continue to operate through the distal spine engaging portion of the extended outer sleeve and still maintain the distraction and alignment of the vertebrae.

A spinal implant may then be inserted through the extended outer sleeve and into the hole in the adjacent vertebrae. The extended outer sleeve is removed once the spinal implant has been inserted. If the spinal implant being inserted has surface projections such as a thread, then an inner sleeve is inserted in the extended outer sleeve prior to drilling to accommodate the height of the projections or as in the case of a thread, the difference between the major and minor diameters of the implant.

To further stabilize the spinal implant, a staple alignment rod may be mechanically coupled to the spinal implant prior to the removal of the extended outer sleeve. The extended outer sleeve is then removed and a staple having spine engaging prongs is inserted via the alignment rod and is coupled to the spinal implant. The alignment rod is removed and replaced with a locking screw to secure the staple to the spinal implant.

While the preferred method utilizing a cylindrical implant and involving the removal of some bone from each of the adjacent vertebrae in preparation for fusion has been described, it is understood that the distractor and sleeve could as well be rectangular and the drill supplemented with or replaced by a box chisel, or other chisel so as to produce a rectangular fusion site or similarly any of a variety of shapes. Further, it is understood that the outer sleeve could be dimensioned so as to confine the removal of the disc material, regardless of the means, to the area between the adjacent vertebrae rather than providing for the removal of the bone as well.

OBJECTS OF THE PRESENT INVENTION

It is an object of the present invention to provide instrumentation for performing surgery on the thoracic spine through the chest cavity from a lateral approach to the spine.

It is another object of the present invention to provide a method of performing surgery on the thoracic spine through the chest cavity from a lateral approach to the spine that is safer, more effective and faster than previously possible.

It is a further object of the present invention to provide instrumentation and method of inserting a spinal implant in a hole drilled across the disc space and into two adjacent vertebrae of the thoracic spine through the chest cavity from a lateral approach to the spine.

It is another object of the present invention to provide for a method and instrumentation for performing a thoracic discectomy, an interbody fusion, and rigid internal fixation of the spine through the chest cavity from a lateral approach and all as a single integrated procedure.

It is yet another object of the present invention to provide for a method and instrumentation for performing a lumbar fusion from the lateral aspect of the spine.

It is further another object of the present invention to provide for a method and instrumentation for performing a lumbar fusion and spinal canal decompression from the lateral aspect of the spine.

It is further still another object of the present invention to provide for a method and instrumentation for performing a lumbar fusion, decompressive discectomy, and a rigid internal fixation of the spine and all as a single integrated surgical procedure.

It is further yet another object of the present invention to provide for a method and instrumentation to achieve discectomy, fusion and interbody stabilization of the lumbar without the need to mobilize the great vessels from the front of the vertebral bodies.

These and other objects of the present invention will become apparent from a review of the accompanying drawings and the detailed description of the drawings.

BRIEF DESCRIPTION OF THE DRAWINGS

FIG. 18 is a front elevational view of the segment of the thoracic spine of FIG. 3 showing the extended outer sleeve inserted from a lateral approach to the thoracic spine and seated in the disc space and engaging the two adjacent vertebrae, an implant driver, and a spinal implant about to be inserted through the extended outer sleeve and into the hole drilled across the disc space and into the adjacent vertebrae.

FIG. 19 is a front elevational view of the segment of the thoracic spine of FIG. 3 showing the extended outer sleeve inserted from a lateral approach to the thoracic spine and seated in the disc space and engaging the two adjacent vertebrae and a spinal implant implanted in the hole drilled across the disc space and into two adjacent vertebrae.

FIG. 20 is a front elevational view of the segment of the thoracic spine of FIG. 3 showing the extended outer sleeve inserted from a lateral approach to the thoracic spine and seated in the disc space and engaging the two adjacent vertebrae and an extractor cap for removing the extended outer sleeve about to be coupled to the extended outer sleeve.

FIG. 21 is an enlarged partial sectional view of the extractor cap engaging the extended outer sleeve.

FIG. 22 is a front elevational view of the segment of the thoracic spine of FIG. 20 with the distractor puller coupled to the extractor cap shown removing the outer sleeve from the disc space and the adjacent vertebrae in the direction of the arrow.

FIG. 23 is an enlarged front elevational view of a segment of the thoracic spine having a portion of the top vertebrae removed and a portion of the disc space removed and a spinal implant implanted from a lateral approach to the thoracic spine in the hole drilled across the disc space and into the two adjacent vertebrae.

FIG. 24 is a front elevational view of a segment of the thoracic spine having a spinal implant implanted from a lateral approach to the thoracic spine into a hole drilled across the disc space and into the adjacent vertebrae with a spinal fixation device coupled to the spinal fusion implant and engaging the adjacent vertebrae to lock the spinal implant in place.

FIG. 25 is a side perspective view of an alternative embodiment of the extended outer sleeve of the present invention having a pair of extension members and a pair of prongs.

FIG. 26 is a top plan view of the extended outer sleeve of FIG. 25 shown in partial cutaway with an inner sleeve and a drill inserted within its interior and placed adjacent to a vertebra of the spine with the major vessels and the dural sac and spinal nerves proximate to the vertebra shown in cross section.

FIG. 27 is an anterior elevational view of a vertebra of the spine with the extended outer sleeve of FIG. 25 shown inserted from the lateral approach and seated in the disc space and engaging the vertebra.

FIG. 28 is a posterior elevational view of a vertebra of the spine with the extended outer sleeve of FIG. 25 shown inserted from the lateral approach of the spine and seated in the disc space and engaging the vertebra.

FIG. 35 is a perspective side view of an alternative embodiment of the extended outer sleeve of the present invention having a removable distal end with a single extension member and a pair of prongs.

DETAILED DESCRIPTION OF THE DRAWINGS

Figure 1:
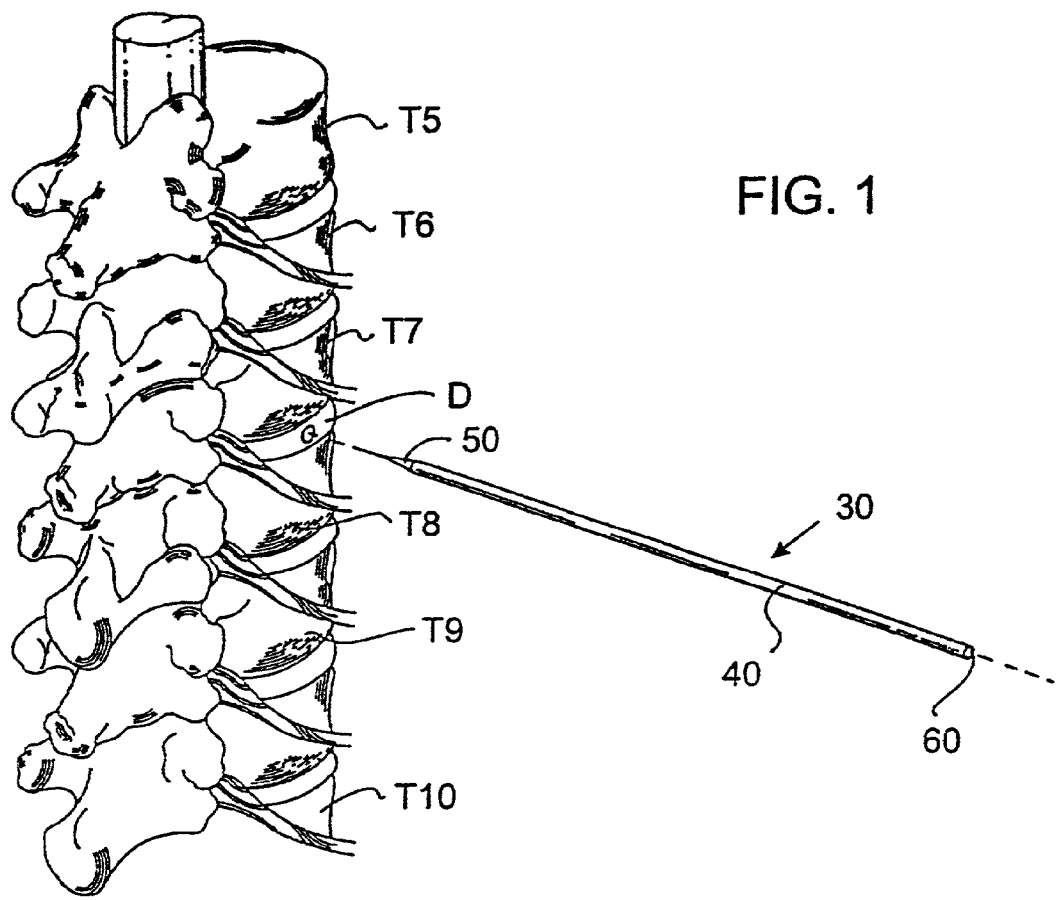
FIG. 1 is a rear perspective view of a segment of the thoracic spine with the guide pin of the present invention about to be inserted from a lateral approach to the thoracic spine into the disc space between two adjacent vertebrae.

Referring to FIG. 1, a rear perspective view of a segment of the thoracic spine S is shown with a guide pin 30 about to be inserted from a lateral approach (through the lateral chest wall) to the thoracic spine S into the disc space D between two adjacent vertebrae, for example vertebrae $T_7$ and $T_8$. The guide pin 30 may first be used as radiological marker to confirm the correct disk level and instrument position, and then functions to align and guide the insertion of the instrumentation described below into the disc space D. The guide pin 30 is inserted through a small incision on the side of a patient's chest cavity perpendicular to the lateral aspect of the vertebrae $T_7$ and $T_8$ of the thoracic spine S. The guide pin 30 is made of a material appropriate for surgical use and comprises a shaft portion 40, a tip 50 which may be pointed to facilitate insertion into the disc space D, and a distal end 60. In the preferred embodiment, the guide pin has a diameter in the range of 1.5 mm to 5.0 mm, with 2.5 mm being the preferred diameter, and a length in the range of 200 mm to 800 mm, with 350 mm being the preferred length.

Figure 2:
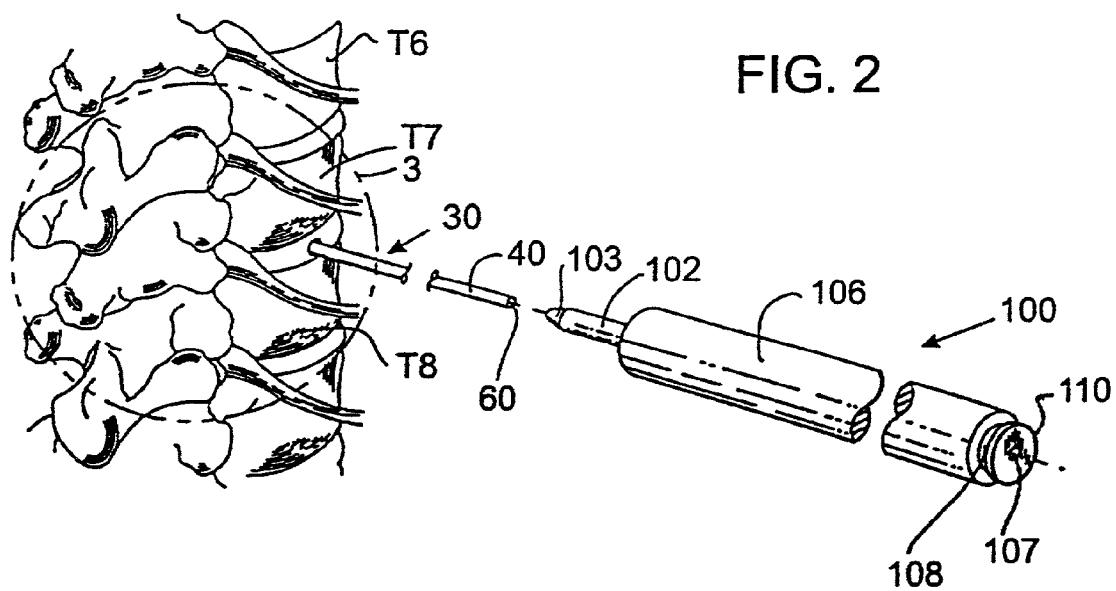
FIG. 2 is a rear perspective view of a segment of the thoracic spine with the guide pin inserted in the disc space between two adjacent vertebrae and the distractor of the present invention about to be placed over the guide pin.
Figure 3:
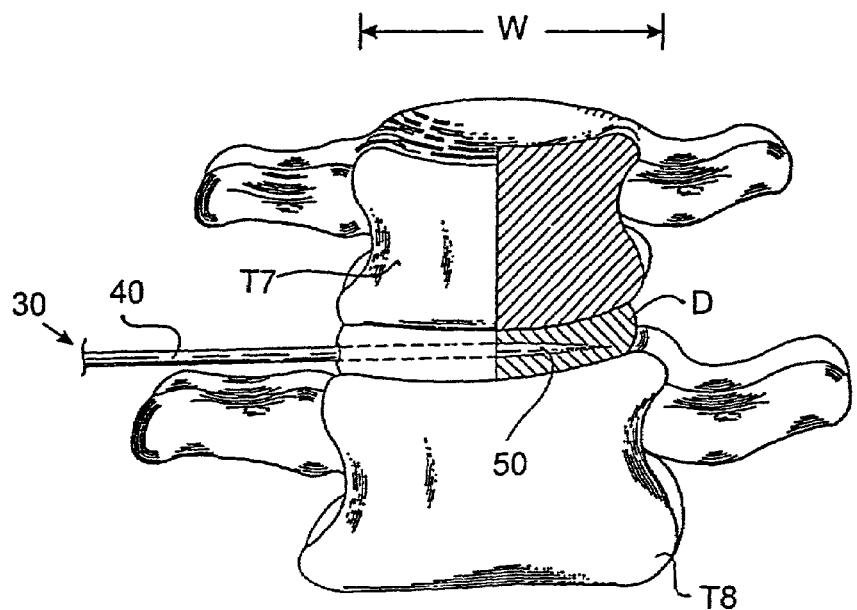
FIG. 3 is an enlarged front elevational view of a segment of the thoracic spine along line 3 of FIG. 2 having a portion of the top vertebrae removed and a portion of the disc removed with the guide pin, shown partially in hidden line, inserted from a lateral approach to the thoracic spine into the disc space.

Referring to FIGS. 2 and 3, the guide pin 30 is shown inserted from a lateral approach to the thoracic spine S and into the disc space D between adjacent vertebrae $T_7$ and $T_8$, with a substantial part of the shaft portion 40 of the guide pin 30 remaining external to the disc space D and functions as a guide post. The tip 50 of the guide pin 30 may penetrate the disc space D for a substantial part of the transverse width W of the vertebrae $T_7$ and $T_8$ such that at least a part of the shaft portion 40 is within the disc space D. The guide pin 30 is firmly embedded in the discal material present within the disc space D, but does not protrude through the opposite side of the disc space D to prevent any unwanted damage to that area. The guide pin 30 is placed in the disc space D so that it is parallel to the end plates of the vertebrae $T_7$ and $T_8$, and centered within the disc space D to bisect the disc space D along the transverse width W of the vertebrae $T_7$ and $T_8$. In this manner, a substantial portion of the vertebrae $T_7$ and $T_8$ is present near the circumference of the guide pin 30 such that instruments having a diameter greater than the guide pin 30 may be inserted into the vertebrae $T_7$ and $T_8$ coaxial to the guide pin 30 without protruding from the vertebrae $T_7$ and $T_8$. Such instruments are guided and aligned during insertion by the guide pin 30 so that they are correctly oriented with respect to the vertebrae $T_8$ and $T_8$. The surgeon may monitor the correct orientation of the guide pin 30 within the disc space D indirectly with an image intensifier, or directly with a thorascope if one is being used.

Once inserted in the disc space D, the guide pin 30 functions as a guide post for a distractor 100 which is placed over the guide pin 30 and inserted in the disc space D to distract the disc space D and align the adjacent vertebrae $T_7$ and $T_8$ by urging them apart. Circumstances permitting, the surgeon may elect to bypass the use of the guide pin 30 and insert the distractor 100 directly. The distractor 100 has a cylindrical barrel 106 that terminates at one end in a reduced diameter disc penetrating portion 102 that is essentially cylindrical, with a further reduced diameter, bullet-shaped front end 103 to facilitate insertion into the disc space D. The distractor 100 has a shoulder portion 104 where the penetrating portion 102 extends from barrel 106 and has a hollow longitudinal passageway 107 extending the entire length of the distractor 100 for receiving the guide pin 30. The passageway 107 of the distractor 100 is open at both ends of the distractor 100 and has a diameter that is slightly greater than the diameter of the shaft portion 40 of guide pin 30. The shaft portion 40 of the guide pin 30 may pass through the passageway 107 as the distractor 100 is placed coaxially over the guide pin 30. In this manner, the distractor 100 can be guided and aligned by the guide pin 30 so that it is inserted into the disc space D coaxial to the guide pin 30 and is properly aligned with respect to the vertebrae $T_7$ and $T_8$. Once the distractor 100 is properly placed within the disc space D, the guide pin 30 may be removed from the disc space D through the passageway 107 of the distractor 100.

The appropriate placement of distractor 100 in the disc space D may be determined visually by the surgeon by the use of a thorascope and or by the use of radiographic, fluoroscopic, or similar procedures; such as utilizing an image intensifier, all of which allow the surgeon to determine the correct orientation and placement of the guide pin 30 and distractor 100 within the disc space D. The correct orientation and placement of the distractor 100 is important to the success of the method of the present invention, as the purpose of the distractor 100 is to space part and align the vertebrae $T_7$ and $T_8$ and to guide the insertion into the disc space D of the extended outer sleeve 140 described in detail below. As the diameter of the distractor 100 is almost the same as the inner diameter of the extended outer sleeve 140 and is the same as the spinal implant I, also described in detail below, the surgeon can use x-rays to determine whether the distractor 100 is properly oriented with respect to the adjacent vertebrae $T_7$ and $T_8$, such that any subsequent drilling through the extended outer sleeve 140 and insertion of spinal implant I will be correctly oriented with respect to the vertebrae $T_7$ and $T_8$. Such a precaution will permit the surgeon to correct any misplacement of the distractor 100 before any irreversible drilling or implant insertion has occurred.

The penetrating portion 102 of the distractor 100 may be of various diameters and lengths, the preferred length being less than the known transverse width W (side to side) of the vertebrae $T_7$ and $T_8$. This combined with the circumferential shoulder portion 104 of the distractor 100, which is too large to fit within the disc space D, protects against the danger of over penetration. The barrel 106 of the distractor 100 may have at its distal end a recessed portion 108 below the crown 110 which allows for the distractor 100 to be engaged by an extractor unit shown in FIG. 9.

In the preferred embodiment of the distractor 100, the barrel 106 has a diameter in the range of 10 mm to 30 mm, with 20 mm being the preferred diameter, and the penetrating portion 102 has a diameter in the range of 3 mm to 10 mm, with 6 mm being the preferred diameter.

Figure 4:
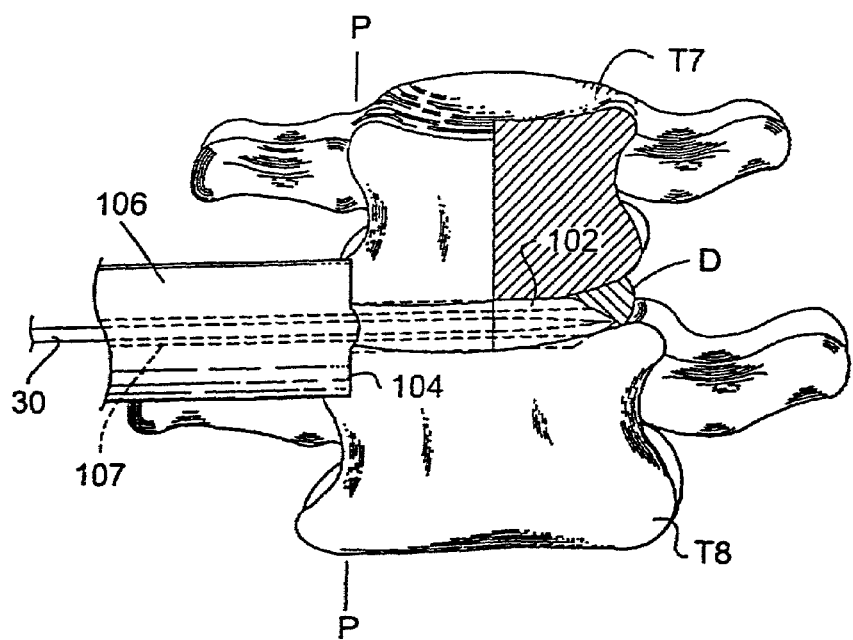
FIG. 4 is an enlarged front elevational view of the segment of the thoracic spine of FIG. 3 with the guide pin and distractor, shown partially in hidden line, inserted from a lateral approach to the thoracic spine in the disc space.
Figure 5:
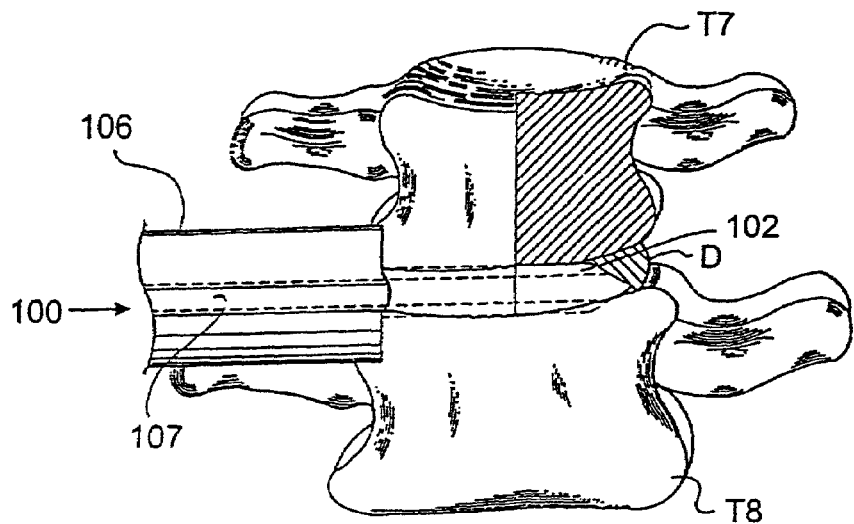
FIG. 5 is an enlarged front elevational view of the segment of the thoracic spine of FIG. 3 with the distractor, shown partially in hidden line, inserted from a lateral approach to the thoracic spine and seated in the disc space and the guide pin removed.

Referring to FIGS. 4 and 5, once the distractor 100 is inserted into the disc space D, the penetrating portion 102 of the distractor 100 distracts the vertebrae $T_7$ and $T_8$ apart, such that the vertebrae $T_7$ and $T_8$ to either side of the penetrating portion 102 are forced into full congruence and thus become parallel, not only to the penetrating portion 102, but to each other. Because of the forced opposition of the vertebrae $T_7$ and $T_8$ to the penetrating portion 102 the distractor 100 will then come to lie absolutely perpendicular to the plane P of the lateral aspect of the thoracic spine S and absolutely parallel to the vertebral endplates, allowing optimal alignment for the procedure to be performed.

Figure 6:
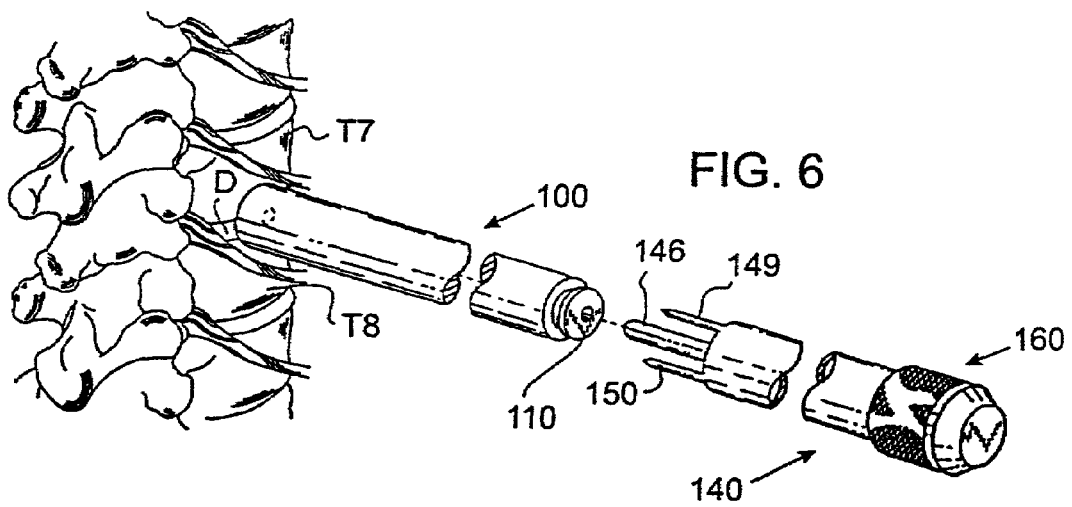
FIG. 6 is a rear perspective view of a segment of the thoracic spine having a distractor inserted from a lateral approach to the thoracic spine and seated in the disc space and the extended outer sleeve of the present invention coupled to a driver cap and about to be placed over the distractor.
Figure 7:
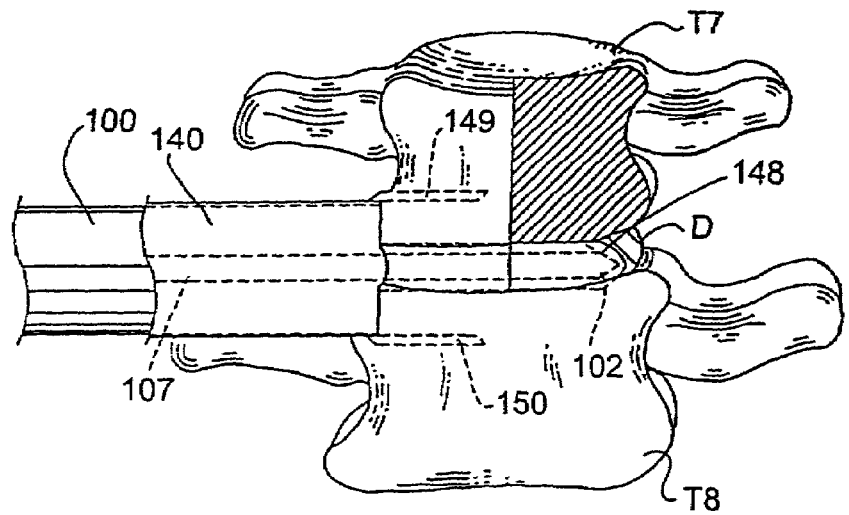
FIG. 7 is an enlarged front elevational view of the segment of the thoracic spine of FIG. 3 with the distractor and the extended outer sleeve inserted from a lateral approach to the thoracic spine and seated in the disc space.
Figure 7A:
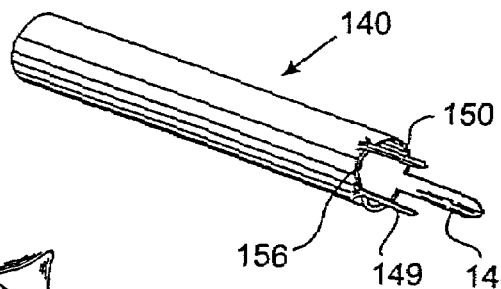
FIG. 7A is side perspective view of the extended outer sleeve of the present invention.

Referring to FIGS. 6, 7 and 7A, the distractor 100 now serves as both a centering post and an alignment rod for the extended outer sleeve 140 which is fitted over the distractor 100 and inserted into the disc space D. As shown in FIG. 7A, the extended outer sleeve 140 is a hollow tubular member made of material appropriate for surgical use and preferably metal, and has an inner diameter sufficiently sized to receive the distractor 100. The inner diameter of the extended outer sleeve 140 closely matches the outer diameter of the distractor 100, so that a close fit is achieved and the extended outer sleeve 140 is precisely guided by the distractor 100. The extended outer sleeve 140 has at its distal end 146 an extension member 148 and two prongs 149 and 150 sufficiently spaced apart to penetrate and hold fixed the two adjacent vertebrae $T_7$ and $T_8$. The extension member 148 is essentially a continuation of the extended outer sleeve 140 and the prongs 149 and 150 are offset from the extended outer sleeve 140 or can also be a continuation of the extended outer sleeve 140 like extension member 148. The prongs 149 and 150 may have sharp insertion edges 152 and 154 to facilitate insertion into the vertebrae $T_7$ and $T_8$.

Where the surgery is for a disc herniation, the extension member 148 of the extended outer sleeve 140 located anteriorly is used without a second extension member posteriorly, as the use of the two prongs 149 and 150 in conjunction with the anterior extension member 148 makes it possible to operate through the extended outer sleeve 140 posteriorly, without obstruction and with good visibility when an endoscope is used such that any remaining disc herniation may be removed. The extension member 148 of the extended outer sleeve 140 provides a protective barrier to the structures lying beyond it.

However, if the surgery is not for a disc herniation, but for example, for stabilization of the spine, then the extended outer sleeve may have both an anterior extension member 148 and a corresponding posterior extension member with or without prongs, such as the extended outer sleeve 1100 shown in FIG. 35 and described in greater detail below.

In the preferred embodiment, the extension member 148 of the extended outer sleeve 140 functions to maintain the distraction and alignment of the vertebrae $T_7$ and $T_8$, as the extension member 148 is being inserted from the lateral aspect of the thoracic spine S. Without the extension member 148, in order to maintain the proper distraction of the adjacent vertebrae $T_7$ and $T_8$, it would be necessary to place a surgical instrument, such as a second distractor (not shown) on the opposite side of the vertebrae $T_7$ and $T_8$. This would require a second incision in the opposite side of the patient's chest cavity for insertion of the required surgical instruments. Further, as it is desired to insert an implant of the maximum possible length across the transverse width W of the vertebrae $T_7$ and $T_8$, the presence of any instrumentation at the opposite end of the vertebrae $T_7$ and $T_8$, would interfere with the insertion of such an implant. For example, the second distractor on the opposite side of the vertebrae $T_7$ and $T_8$ would be in the way of a drill used to create a hole across the transverse width W of the vertebrae $T_7$ and $T_8$, since the drilled opening would overlap the second distractor. Therefore, the extension member 148 solves the problem of maintaining an even distraction of the two adjacent vertebrae $T_7$ and $T_8$ across their transverse width W from only one side of the thoracic spine S, allowing for the unimpeded insertion of instruments and/or implants. While in the preferred embodiment, the extended outer sleeve 140 has an extension member 148, it is also possible to have an extended outer sleeve without any extension members and instead, having prongs of sufficient length that engage the bone of the adjacent vertebrae to maintain the distraction and alignment of the adjacent vertebrae created by the distractor 100. However, the use of such an extended outer sleeve capable of holding, but not of obtaining, the desired intervertebral distraction and alignment would require the use of a distractor prior to its insertion as earlier described herein.

In the preferred embodiment of the extended outer sleeve 140, a single extension member 148 is present and oriented anteriorly to protect the major vessels located to the anterior aspect of the thoracic spine S. The extended outer sleeve 140 has no extension member near the posterior aspect the spine as it is often necessary to access the spinal canal in order to remove any diseased discal material. In the special circumstances where only vertebral fusion is desired, the extended outer sleeve 140 may have a second extension member (not shown) identical to the extension member 148 positioned diametrically opposite the extension member 148 in order to protect the spinal canal, and in such instance may or may not have the bone penetrating prongs 149 and 150.

The extension member 148 of the extended outer sleeve 140 has a height that is generally approximately equal to the diameter of the penetrating portion 102 of the distractor 100, such that the extension member 148 is capable of maintaining the spacing created by the insertion of the distractor 100 between the adjacent vertebrae $T_7$ and $T_8$ which is generally the restoration to normal of the disc space D. The extension member 148 is tapered at its leading edge 151 to facilitate insertion into the disc space D and is positioned approximately 120 degrees from each of the two prongs 149 and 150. The extension member 148 of the extended outer sleeve 140 works in conjunction with the prongs 149 and 150 which engage the vertebrae $T_7$ and $T_8$, respectively, to maintain the distraction and alignment of the vertebrae $T_7$ and $T_8$. Further, the prongs 149 and 150 not only hold the vertebrae $T_7$ and $T_8$ apart, but during drilling also help to hold them together so as to resist them moving apart.

In the preferred embodiment, the extension member 148 of the extended outer sleeve 140 has a length that is less than the transverse width w of the vertebrae $T_7$ and $T_8$. The extension member 148 needs to be relatively long because it must maintain distraction of the adjacent vertebrae $T_7$ and $T_8$ when placed across the transverse width W of the vertebrae $T_7$ and $T_8$. Therefore, if the extension member 148 is shorter than one half the transverse width W of the vertebrae $T_7$ and $T_8$, it may not be capable of distracting and aligning the vertebrae $T_7$ and $T_8$, and a second distractor would be required as described above, to achieve the correct distraction and alignment of the vertebrae $T_7$ and $T_8$.

In the preferred embodiment, the extended outer sleeve 140 has an outer diameter in the range of 12 mm to 34 mm, with 24 mm being the preferred outer diameter, and an inner diameter in the range of 10 mm to 28 mm, with 20 mm being the preferred inner diameter of the extended sleeve 140.

In the preferred embodiment, the extension member 148 of the extended outer sleeve 140 has a length in the range of 14 mm to 30 mm, with 24 mm being the preferred length, and a height in the range of 3 mm to 10 mm, with 6 mm being the preferred height. In the preferred embodiment, the prongs 149 and 150 of the extension member 140 have a length in the range of 6 mm to 20 mm, with 14 mm being the preferred length and a diameter in the range of 2 mm to 3 mm, with 2 mm being the preferred diameter of the prongs 149 and 150.

Referring specifically to FIG. 6, coupled to the proximal end 157 of the extended outer sleeve 140 is a driver cap 160 in the form of an impaction cap which has at its far end a flat, closed-back surface 162 and at its other end a broad, circular opening. The driver cap 160 is used for driving the extended outer sleeve 140 toward the vertebrae $T_7$ and $T_8$ and fits over both the extended outer sleeve 140 and the distractor 100. An impaction force, such as a mallet blow, is applied to surface 162 of the driver cap 160 to advance the extended outer sleeve 140. That force is transmitted to the extended outer sleeve 140 via its proximal end 157, seating the prongs 149 and 150 of the extended outer sleeve 140 into the vertebrae $T_7$ and $T_8$ and inserting the extension member 148 into the disc space D. As the extended outer sleeve 140 is advanced forward, the crown 110 of the distractor 100 is allowed to protrude within the driver cap 160 unobstructed until it contacts the interior of the driver cap 160, such that further taps of the mallet will not further advance the extended outer sleeve 140. Any further motion is resisted by the flat shoulder portion 104 of the distractor 100 abutting the hard lateral outer surfaces of the adjacent vertebrae $T_7$ and $T_8$. The flat, planar area 156 of the distal end 146 of extended outer sleeve 140 serves to resist the further insertion of the extension member 148 into the disc space D and to resist further insertion of the prongs 149 and 150 into the vertebrae $T_7$ and $T_8$. In this way, the extended outer sleeve 140 is safely and assuredly inserted to its optimal depth, and no further, and rigidly secures the two adjacent vertebrae $T_7$ and $T_8$ as shown in FIG. 7.

Figure 8:
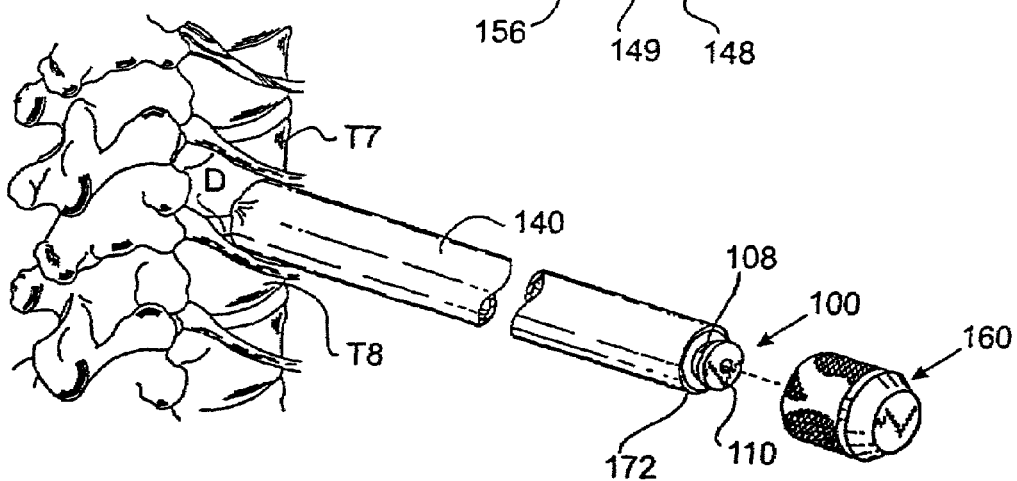
FIG. 8 is a rear perspective view of a portion of the thoracic spine with the extended outer sleeve fully seated over the distractor inserted from a lateral approach to the thoracic spine and seated in the disc space and with the driver cap removed.
Figure 9:
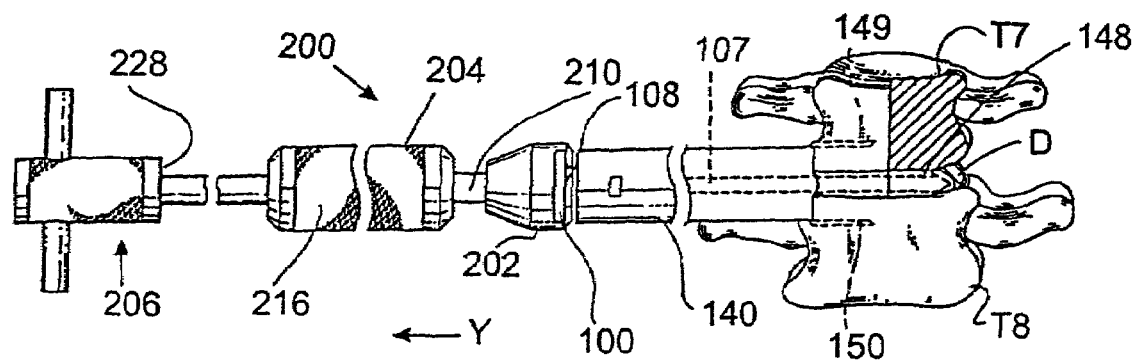
FIG. 9 is a front elevational view of a segment of the thoracic spine of FIG. 3 with the extended outer sleeve inserted from a lateral approach to the thoracic spine and seated in the disc space and engaging the adjacent vertebrae showing the distractor being removed by a distractor puller.

Referring to FIGS. 8 and 9, the driver cap 160 is then removed and the crown 110 and the recessed portion 108 of the distractor 100 protrude from the proximal end 157 of the extended outer sleeve 140. The distractor 100 may now be removed from within the extended outer sleeve 140 since the extended outer sleeve 140 functions to maintain the distraction and alignment of the vertebrae $T_7$ and $T_8$. The extended outer sleeve 140 is held secure by the extension member 148 inserted within the disc space D and by the prongs 149 and 150 engaging the vertebrae $T_7$ and $T_8$.

A distractor puller 200 is utilized to remove the distractor 100 in the direction of arrow Y from within the disc space D leaving the extended outer sleeve 140 in place. The distractor puller 200 has front portion 202, a mid portion 204, and a back handle portion 206. The front portion 202 of the distractor puller 200, is connected to one end of shaft 210 which at its far end is connected to the back handle portion 206. The distractor puller 200 is described in detail in copending application Ser. No. 08/074,781, entitled APPARATUS AND METHOD FOR INSERTING SPINAL IMPLANT, and is incorporated herein by reference. The socket-like front portion 202 of the distractor puller 200 engages the circumferential recessed portion 108 of the distractor 100.

A cylindrical and freely movable weight 216 is fitted around shaft 210 between the front portion 202 and the rear handle portion 206 of the distractor puller 200 so as to form a slap hammer. The weight 216 of the distractor puller 200 is gently and repeatedly slid along the shaft 210 and driven rearwardly against flat surface 228 of the rear handle portion 206 to transmit a rearward vector force to front portion 202 and to the distractor 100 to which it is engaged. In this manner, the distractor 100 is removed from within the disc space D and out of the extended outer sleeve 140 without disturbing it.

Figure 10:
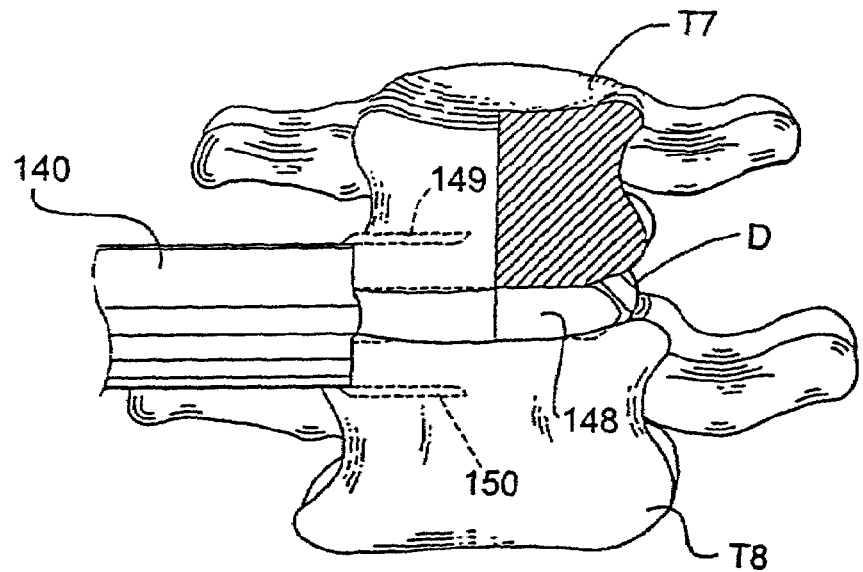
FIG. 10 is an enlarged front elevational view of the segment of the thoracic spine of FIG. 3 with the extended outer sleeve inserted from a lateral approach to the thoracic spine and seated in the disc space and engaging the two adjacent vertebrae.

Referring to FIG. 10, once the distractor 100 has been completely removed from within the extended outer sleeve 140 and from within the disc space D, the extension member 148 remains within the disc space D and the prongs 149 and 150 rigidly maintain the appropriate distraction and the relative position of the adjacent vertebrae $T_7$ and $T_8$. The remainder of the procedure occurs entirely through the extended outer sleeve 140 and the space therein is sealed off from any of the organs of the chest.

Figure 11:
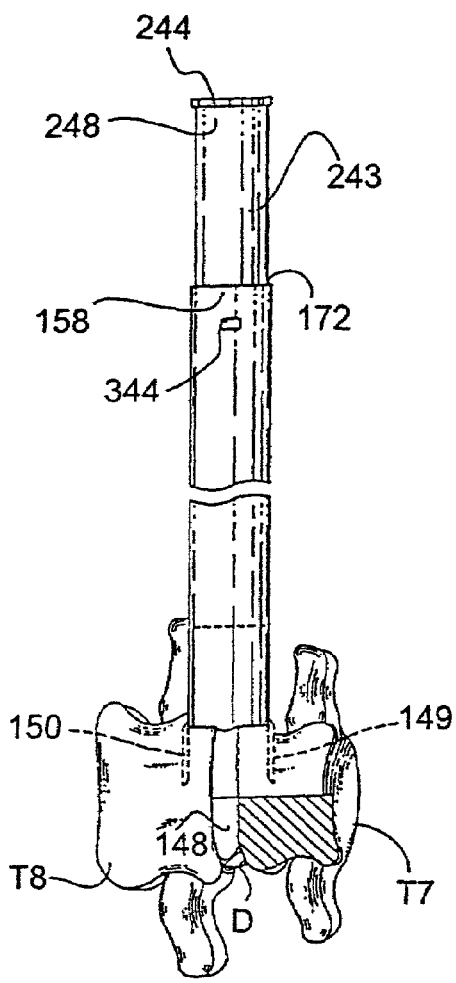
FIG. 11 is a front elevational view of a segment of the thoracic spine of FIG. 3 with the inner sleeve of the present invention being inserted into the extended outer sleeve.
Figure 12:
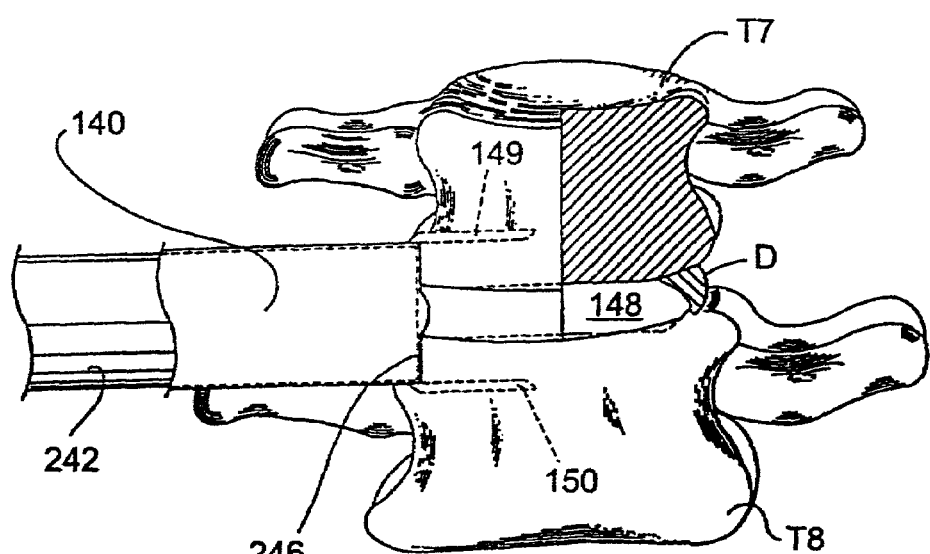
FIG. 12 is an enlarged front elevational view of the segment of the thoracic spine of FIG. 3 with the inner sleeve, shown in partial hidden line, inserted into the extended outer sleeve that is inserted from a lateral approach to the thoracic spine in the disc space and engages two adjacent vertebrae.

Referring to FIGS. 11 and 12, since the extended outer sleeve 140 is of a fixed length and rigid, the flat rearward surface 172 of the distal end 146 may be used as a stop to the advancement of any instruments placed through the extended outer sleeve 140, thus protecting against accidental over penetration. Further, the extended outer sleeve 140 assures that the further procedure to be performed will occur coaxial to the disc space D and further, be symmetrical in regard to each of the adjacent vertebrae $T_7$ and $T_8$.

Where it is desirable to drill a hole smaller in diameter than the spinal implant to be inserted, such as in the case where the spinal implant is threaded, an inner sleeve 242 which functions as a drill guide and spacer having a thickness which corresponds to the difference between the major and minor diameters of the spinal implant, is inserted in the proximal end 158 of the extended outer sleeve 140. The inner sleeve 242 is a hollow tubular member comprising a barrel portion 243 and a cuff portion 244 having a greater outer diameter than the barrel portion 243. The cuff portion 244 of the inner sleeve 242 seats against the flat rearward surface 172 of the extended outer sleeve 140 to prevent further insertion of the inner sleeve 242. The distal end 246 of the inner sleeve 242 extends towards but does not impact the lateral aspect of the adjacent vertebrae $T_7$ and $T_8$ in the interior of the extended outer sleeve 140 when fully seated. The barrel portion 243 of the inner sleeve 242 has an outer diameter that fits within the inner diameter of the extended outer sleeve 140. In the preferred embodiment, the barrel portion 243 of the inner sleeve 242 has an outside diameter in the range of 10 mm to 28 mm, with 20 mm being the preferred outer diameter, and a wall thickness in the range of 0.5 mm to 3 mm, with approximately 0.75 to 1.5 mm being the preferred thickness.

Figure 13:
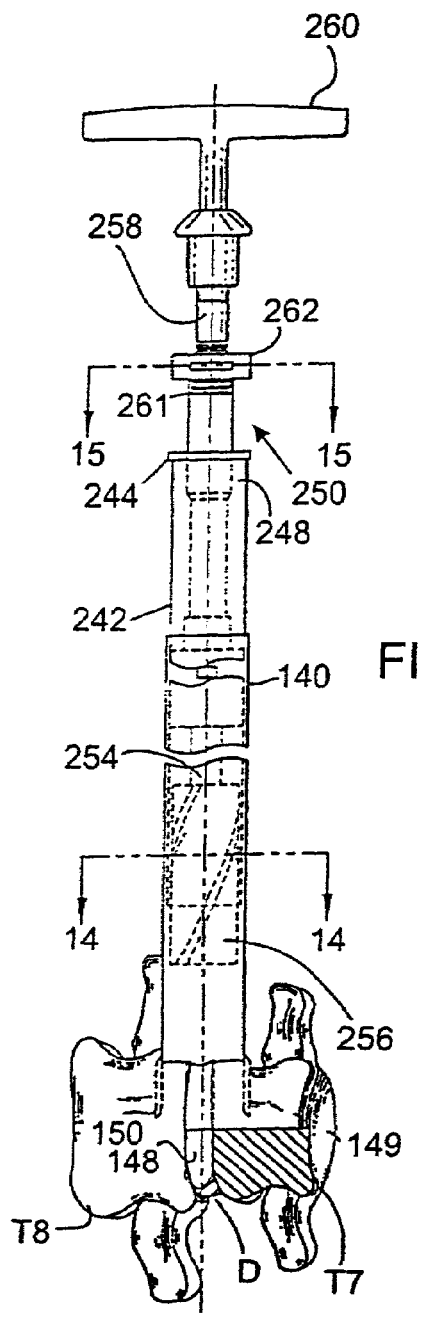
FIG. 13 is a side elevational view of a segment of the thoracic spine of FIG. 3 showing the extended outer sleeve inserted from a lateral approach to the thoracic spine in the disc space and engaging the two adjacent vertebrae with the inner sleeve and drill shown in an exploded view and partially in hidden line.
Figure 15:
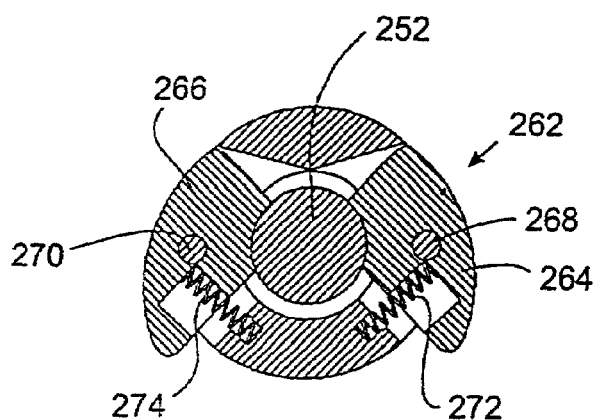
FIG. 15 is a cross sectional view along lines 15—15 of FIG. 13 of the collar for limiting the drilling depth of the drill.
Figure 14:
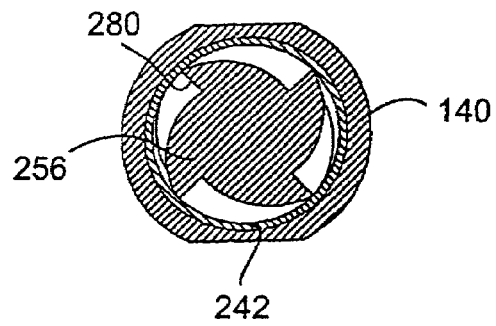
FIG. 14 is a cross sectional view along lines 14—14 of FIG. 13 of the drill, inner sleeve and extended outer sleeve.
Figure 16:
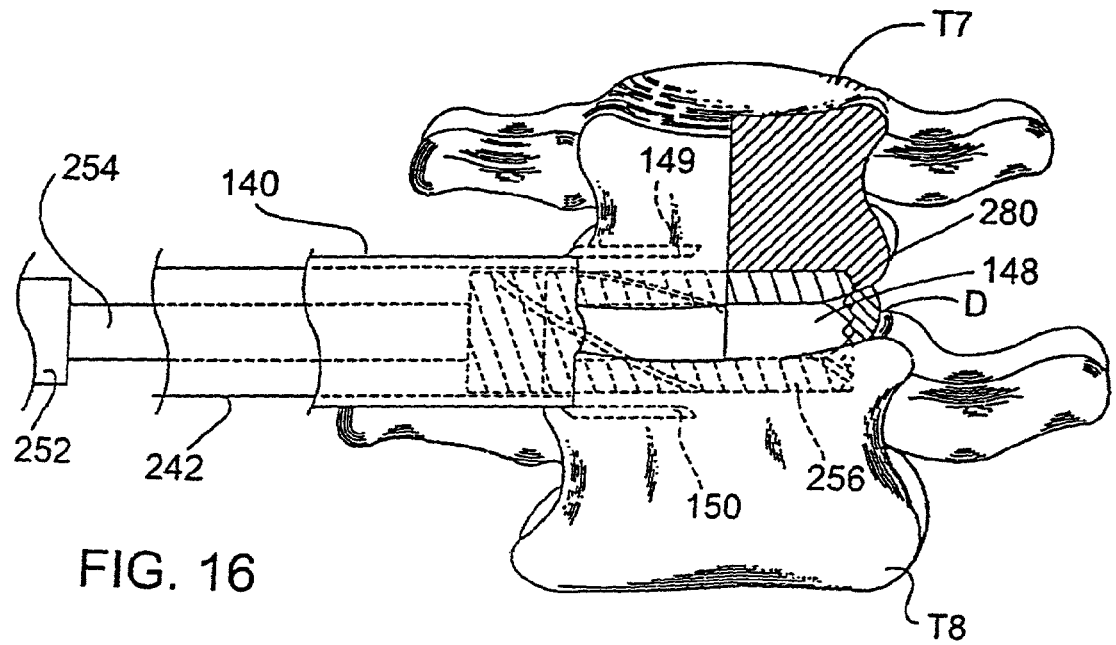
FIG. 16 is an enlarged front elevational view of the segment of the thoracic spine of FIG. 3 showing the extended outer sleeve inserted from a lateral approach to the thoracic spine and seated in the disc space and engaging the two adjacent vertebrae, the inner sleeve inserted in the extended outer sleeve, and the drill passing through the inner sleeve to create a hole across the disc space and into the adjacent vertebrae.

Referring to FIGS. 13–15, once the inner sleeve 242 is seated within the extended outer sleeve 140, a drill 250 connected to a handle 260 or to a drill motor (not shown), is introduced through the aperture in the proximal end 248 of the inner sleeve 242 and utilized to create a hole across the disc space D and into the adjacent vertebrae $T_7$ and $T_8$. The drill 250 reams out arcs of bone which it engages from the adjacent vertebrae $T_7$ and $T_8$, as well as any discal material within its path down to its predetermined and limited depth. It is appreciated that if an inner sleeve 242 is not used, the drill 250 may be placed directly into the extended outer sleeve 140 to create a hole across the disc space D and into the adjacent vertebrae $T_7$ and $T_8$.

The drill shaft of drill 250 comprises an upper portion 252, a central recessed portion 254 of a smaller diameter and a lower cutting portion 256. The drill 250 has a narrow engagement portion 258, which allows it to be affixed to a driving mechanism which may be either a manual unit such as, handle 260, or a power unit such as an electric drill motor. The upper portion 252 has a plurality of grooves 261 for engaging a circumferential collar 262 of an increased diameter which serves to limit the depth of penetration of the drill 250 and may be fixed, or lockably adjustable.

Referring to FIG. 15, a cross sectional view of the circumferential collar 262 is shown engaging the upper portion 252 of the shaft of drill 250. The collar 262 comprises diametrically opposite first and second flanges 264 and 266. The first and second flanges 264 and 266 are pivotably attached to the collar 262 by first and second pins 268 and 270 and spring biased by first and second spring 272 and 274. The first and second flanges 264 and 266 of the collar 262 are contoured to correspond to the curvature of the upper portion 252 of the drill 250. The first and second flanges 264 and 266 engage one of the grooves 261 when in the full biased position as shown in FIG. 15. To disengage the grooves 261, the first and second 264 and 266 are compressed together by the surgeon such that the first and second springs 272 and 274 are compressed and the first and second flanges 264 and 266 pivot away from the upper portion 252 of the shaft, such that the collar 262 can slide along the upper portion 252 of the drill 250. The first and second flanges 264 and 266 of the collar 262 are oriented opposite each other and need to be compressed together in order to disengage the grooves 261. The compression of one of the flanges 264 and 266 alone will not disengage the collar 262 from the grooves 261. In this manner, collar 262 can not become accidentally disengaged during the rotation of the drill 250.

While it is believed that this mechanism is entirely novel, it is appreciated that various mechanisms to lockably adjust drills are well-known to those skilled in the art. Such mechanisms include, but are not limited to, the use of collets, threaded shafts with lock nuts, and flanges engaging grooves forced therein by either a cap pulled over the flanges or screwed down upon them.

Referring to FIGS. 13 and 14, in the preferred embodiment, the forward cutting edge 280 of drill 250 is a four cutting edge end mill modification of a large fluted drill design. The cutting portion 256 of the drill 250 resembles an end cutting mill which may contain any workable number of cutting surfaces, but preferably four or more, that are relatively shallow such that the advancement of the drill 250 occurs more slowly. The cutting portion 256 of the drill 250 may be of a different diameter depending on the type of spinal implant that is being inserted. If the spinal implant being inserted is threaded, the outside diameter of the cutting portion 256 of the drill 250 would generally correspond to the minor diameter of the threaded implant. The inner sleeve 242 has an inner diameter slightly greater than the minor diameter of a threaded implant and its outer diameter is slightly smaller than the inside diameter of the extended outer sleeve 140 which has the same outer diameter as the major diameter (with threads) of the threaded implant. If the implant is not threaded, the outside diameter of the drill 250 corresponds to the inside diameter of the extended outer sleeve 140 such that a hole the maximum diameter of the extended outer sleeve may be drilled.

The inner sleeve 242 serves many functions. First, it provides an intimate drill guide for drill 250 in the event a smaller diameter hole is to be drilled than that of the inside diameter of the extended outer sleeve 140. Second, since the inner sleeve 242 guides the drill 250, it allows for the extended outer sleeve 140 to have an internal diameter large enough to admit a threaded implant, which is larger in diameter than the outer diameter of the drill 240.

If a larger extended outer sleeve 140 were utilized absent the inner sleeve 242, then the drill 250 would be free to wander within the confines of that greater space and would not reliably make parallel cuts removing equal portions of bone from the adjacent vertebrae $T_7$ and $T_8$. Further, the bone removal not only needs to be equal, but must be correctly oriented in three dimensions. That is, the path of the drill 250 must be equally centered within the disc space, parallel the endplates, and perpendicular to the long axis of the spine dissecting the disc space D.

A further purpose of the inner sleeve 242 is that it may be removed simultaneously with the drill 250, thereby trapping the debris, both cartilaginous and bony, generated during the drilling procedure. The debris is guided rearward by the large flutes 251 of the lower cutting portion 256 and is collected around the central recessed portion 254 and then contained and between the recessed portion 254 and the inner wall of the inner sleeve 242. Thus, by removing the drill 250 in conjunction with the inner sleeve 242, much of the debris generated by the drilling procedure is safely removed from the drilling site.

Figure 17:
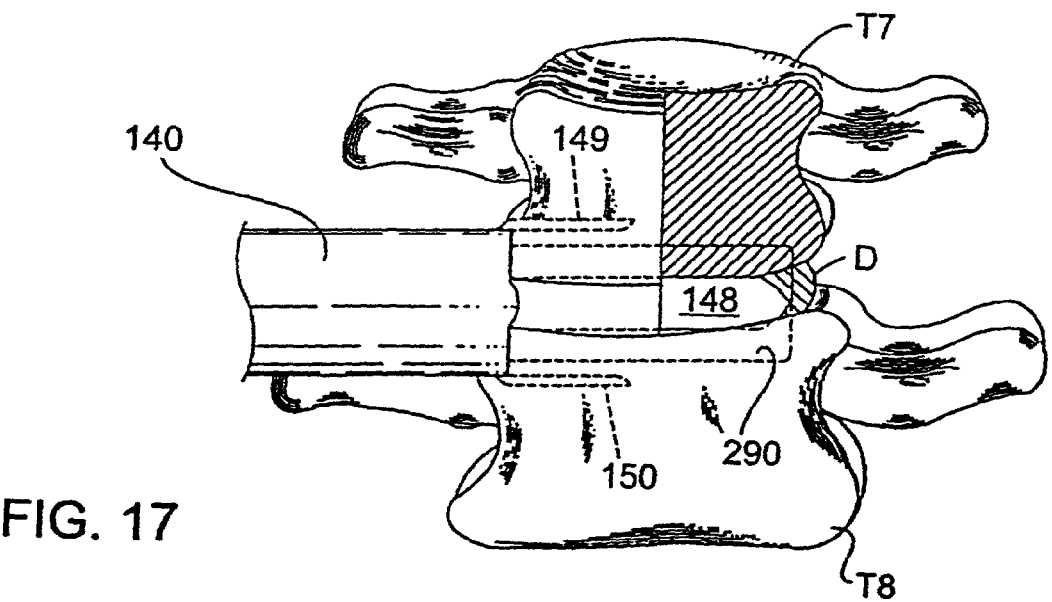
FIG. 17 is an enlarged front elevational view of the segment of the thoracic spine of FIG. 3 with the extended outer sleeve inserted from a lateral approach to the thoracic spine and seated in the disc space and engaging the two adjacent vertebrae illustrating a hole drilled across the disc space and into the adjacent vertebrae.

Referring to FIG. 17, once the drill 250 and the inner sleeve 242 are removed from the extended outer sleeve 140 a cylindrical hole 290 remains across the disc space D and into the two adjacent vertebrae $T_8$ and $T_8$. The cylindrical hole 290 is oriented across the transverse width W of the vertebrae $T_7$ and $T_8$ in which an implant of appropriate diameter is to be implanted. The proper distraction and orientation of the two adjacent vertebrae $T_7$ and $T_8$ is maintained by the extension member 148 and the prongs 149 and 150 of the extended outer sleeve 140.

The cylindrical hole 290 may then be irrigated and vacuumed through the extended outer sleeve 140 to remove any remaining debris from the drilling. If necessary, a thrombin soaked sponge may be inserted through the extended outer sleeve 140 and into the cylindrical hole 290 to coagulate any bleeding. The thrombin soaked sponge is then removed and the surgeon utilizing an endoscope then visually inspects the cylindrical hole 290 for any remaining discal material, and removes any such material requiring such removal with a surgical instrument such as a curette or rongeur.

Referring to FIG. 18, with the extended outer sleeve 140 still in place, the surgical site is now fully prepared to receive a spinal implant I for fusion of the vertebrae $T_7$ and $T_8$. The spinal implant I may be coated with, and/or made of, and/or loaded with substances consistent with bony fusion which may promote bone growth and/or fusion prior to being implanted. Examples of such fusion promoting substances include, but are not limited to, bone, bone morphogenetic protein, hydroxyapatite, hydroxyapatite tricalcium phosphate, and coral. Once the spinal implant I has been prepared for implantation, a driver instrument, such as driver 300 may be used to either insert or to remove spinal implant I. Driver 300 has at its distal end 302, a rectangular protrusion 304, which intimately engages the complimentary rectangular slot in the rear of implant I. Extending from the rectangular protrusion 304 is threaded portion 306, which extends as a rod through hollow shaft 308 and hollow barrel portion 310 to knob 312 where it can be rotationally controlled. Threaded portion 306 screws into a threaded aperture in the spinal implant I and binding them together such that driver 300 can be rotated via paired and diametrically opposed extending arms 314 and 316 and in either direction while maintaining contact with the spinal implant I.

Affixed to the driver 300, the spinal implant I is then introduced through the extended outer sleeve 140 and if the spinal implant I is threaded, screwed into the cylindrical hole 290 between the two vertebrae $T_7$ and $T_8$ until such time as the leading edge of the implant cap 318 reaches the depth of the cylindrical hole 290 at which time its forward motion is impeded by the bone lying before it which had not been drilled out. This allows for a progressive feel to the surgeon as the spinal implant I is inserted into place. It is appreciated that if the spinal implant I is not threaded, instead of being screwed into hole 290, it may be linearly advanced into hole 290 by pushing the driver 300 toward the hole 290.

The terminal resistance to further seating provides significant tactile feedback to the surgeon. Visual monitoring of the depth of insertion of the spinal implant I is provided to the surgeon by observing the progressive approximation of the forward surface 320, of barrel portion 310, as it approaches the rearward facing surface 172 of extended outer sleeve 140 and/or by the use of an image intensifier. As a final safety mechanism, when the full depth of insertion has been achieved, forward surface 320 of instrument 350 will abut surface 172 of the extended outer sleeve 140, prohibiting any further installation of the implant. Once the spinal implant I has been fully installed, the driver 300 is dissociated from the implant by turning knob 312 in a counterclockwise direction. The driver 300 is then withdrawn from the extended outer sleeve 140.

Referring to FIG. 19, the spinal implant I is shown fully installed to the determined depth in the cylindrical hole 290 drilled across the disc space D and into the adjacent vertebrae $T_7$ and $T_8$. The spinal implant I shown comprises a hollow tubular member which in the preferred embodiment is made of an ASTM surgically implantable material, preferably titanium. However, it is appreciated that other implants, cylindrical or partially cylindrical, or of a variety of shapes, and with or without threads or surface roughenings may be used with the instrumentation and method of the present invention.

Referring to FIG. 20 and 21, an extractor cap 340 for removing the extended outer sleeve 140 is shown about to be coupled to the extended outer sleeve 140. The extractor cap 340 engages the proximal end 157 of the extended outer sleeve 140 by spring tabs 342a and 342b on either side of extractor cap 340 which snap-fit into openings 344a and 344b on either side of the extended outer sleeve 140 to lock in place. The extractor cap 340 has a top 346 that is similar in structure to the proximal end of the distractor 100, having a recess portion 350 and a crown portion 352.

Referring to FIG. 22, once the extractor cap 340 is coupled to the extended outer sleeve 140, the distractor puller 200 is coupled to the top 346 of extractor cap 340 to remove the extended outer sleeve 140 from the disc space D and from the adjacent vertebrae $T_7$ and $T_8$ in the direction of the arrow Z.

Referring to FIG. 23, once the extended outer sleeve 140 has been removed, the spinal implant I remains implanted within the cylindrical hole 290 drilled across the disc space D and the implant engages the two adjacent vertebrae $T_7$ and $T_8$.

Referring to FIG. 24, the spinal implant I may be further stabilized with use of a spinal fixation device 400 such as the staple disclosed in copending application Ser. No. 08/219,626 entitled APPARATUS, INSTRUMENTATION AND METHOD FOR SPINAL FIXATION, which is incorporated herein by reference, The spinal fixation device 400 is coupled to the spinal implant I with a locking screw 410 and engages the vertebrae $T_7$ and $T_8$ via prongs 420 and 422. The spinal fixation device 400 functions to stabilize the spinal implant I and prevent any unwanted excursion of the spinal implant I during the spinal fusion process. It is appreciated that prior to removal of the extended outer sleeve 140, a centering post (not shown) may be inserted through the extended outer sleeve 140 and attached to the threaded opening in the back of the spinal implant I. The extended outer sleeve 140 is then removed and the centering post functions as guide to align the spinal fixation device 400 as it is being driven into the vertebrae $T_7$ and $T_8$ as described in detail in the copending application referenced immediately above.

In the above description in regard to the thoracic spine, the surgical procedure has been described as being performed through a hollow tube (extended outer sleeve 140) and with the aid of a thorascope. It is appreciated that there may be circumstances where the surgeon will elect to perform the surgical procedure through an incision, such as a thoracotomy, where direct visualization of the surgical site is possible obviating the need for the thorascope but without diminishing the teaching of the method of the present invention. In such cases, a modification of the extended outer sleeve 140, such as the extended outer sleeve 1100 shown in FIG. 35 and described in detail below, having a detachable distal end may be beneficially utilized by the surgeon. In this manner, the surgeon has direct visualization of the surgical site while the proper distraction and alignment of the adjacent vertebrae is maintained throughout the procedure by the distal end of the extended outer sleeve.

While the present invention has been described in association with the insertion of a threaded spinal implant, it is recognized that other forms of implants may be used with the present method. For example, dowels, made from bone, coral or artificial materials, knurled or irregularly shaped cylinders or spheres, partial cylinders or any other shaped implants that can be introduced through the extended outer sleeve 140, which itself need not be cylindrical may be used.

When such implants are used, it is appreciated that the steps of the method of the present invention described above may be reduced. For example, once the extended outer sleeve 140 has been seated such that the extension portion 148 is inserted in the disc space D and the prongs 149 and 150 engage the adjacent vertebrae, the step of inserting the inner sleeve 242 may be omitted and a drill having a diameter approximating that of the inner diameter of the extended outer sleeve 140 may be used to drill a hole the size of the inner diameter of the extended outer sleeve 140 across the disc space D and into the adjacent vertebrae. Once the drill has been removed, any remaining discal material or debris may be removed by irrigating and vacuuming the hole, and an implant such as a bone dowel or an implant without threads, may be linearly advanced through the extended outer sleeve 140 and implanted into the hole. The extended outer sleeve 140 is then removed in the same manner described above. Where the implant shape is generally not circular, an appropriately shaped chisel may be used by itself or in conjunction with a drill to prepare an opening for the fusion implant that is other than round.

It is further appreciated that it is also within the scope of the present invention to provide a method and instrumentation for the insertion of a spinal implant into the disc space between two adjacent vertebrae, without the drilling away of significant bone from the vertebrae. Such implants may have a height corresponding to the height of a disc space D and may be pushed into the disc space D when distracted once the disc space D has been cleaned out. This type of implant would preferably have in part a rectangular cross section and an extended outer sleeve used for the insertion of such implants would have a corresponding cross section and shape. Further, it is appreciated that the extended outer sleeve and inner sleeve of the present invention may have any shape or size corresponding to the shape and size of the implant to be inserted without departing from the scope of the present invention.

While the above description has been directed to the thoracic spine, the method and instrumentation of the present invention may also be utilized in the lumbar spine. In the preferred method, the surgeon makes a small incision in the abdominal wall and gently dissects his way retroperitoneal to reach the lateral aspect of the spine. As with the thorascopic method described above, the surgeon may use an endoscope within and/or outside of the extended outer sleeve to facilitate the surgery, and thereby require an incision barely larger than the diameter of the extended outer sleeve which itself is not much larger than the implant.

Referring to FIG. 25, an extended outer sleeve 1000 for use with the lateral method in the lumbar spine is shown. The extended outer sleeve 1000 is similar to the extended outer sleeve 140 described above and comprises a hollow tubular member 1002 having a distal end 1010 which is contoured to hug the vertebrae, for example $L_4$ and $L_5$. The extended outer sleeve 1000 has anterior and posterior extension members 1020 and 1022, each having different heights, that are opposed 180 degrees from each other. Also extending from the distal end 1010 may be prongs 1012 and 1014, similar to prongs 149 and 150 described above, for engaging the bone of the adjacent vertebrae $L_4$ and $L_5$. The extension members 1020 and 1022 are tapered at their leading edges 1024 and 1026 respectively, to facilitate insertion.

As shown in FIGS. 26–28, the extended outer sleeve 1000 is designed to be used in approaching the lumbar spine laterally from either side of the spinal column. The extended outer sleeve 1000 by means of its extended portions 1020 and 1022 is capable of correcting those spinal deformities, such as scoliosis or any abnormality of kyphosis or lordosis, occurring specifically from a deformity of the disc. For example, in order to restore lordosis in the lumbar spine, the anterior extension member 1020 is placed anteriorly between the adjacent vertebrae $L_4$ and $L_5$ and the posterior extension member 1022, having a lesser height than the extension member 1020, is placed posteriorly. The greater height of the extension member 1020 relative to the extension member 1022 maintains the anterior portions of the vertebrae $L_4$ and $L_5$ spaced apart at a greater distance than the posterior portions of the vertebrae $L_4$ and $L_5$ producing an angular relationship between the bodies as would exist with naturally occurring physiologic lordosis. Once restored, lordosis is maintained throughout the surgical procedure.

Scoliosis refers to an abnormal curving of the spine when viewed from straight ahead or behind. Since the extension members 1020 and 1022 may be of a specific and constant height throughout their entire lengths, both sides of the disc space D are lifted to exactly the same height, thus eliminating any side to side angular deformity occurring through that disc space.

Referring specifically to FIG. 26, it can be appreciated that the posterior extension member 1022 effectively prevents any injury to the dural sac and neural elements, while the anterior extension member 1020 in a similar fashion, protects the great blood vessels including the aorta, vena cava and the iliac arteries and veins. As the extended outer sleeve 1000 of the present invention is quite stable once inserted, the preferred embodiment is shown as having only two prongs 1012 and 1014, one each to engage each of the adjacent vertebrae $L_4$ and $L_5$. It is, however, understood that the extended outer sleeve 1000 may have more or less prongs or none at all. The distal end 1010 of the tubular member 1002 is contoured adjacent the origin of the anterior and posterior extended members 1020 and 1022 so as to assure an intimate fit between the tubular member 1002 and the vertebrae $L_4$ and $L_5$ adjacent the disc space D to which it is opposed, and for the purpose of confining the surgery to within the extended outer sleeve 1000 and excluding the adjacent soft tissues from potential injury. In the preferred embodiment, the distal end of the tubular member 1002 and the anterior and posterior extended members 1020 and 1022 themselves have been reinforced, that is are thicker than the adjacent tubular member 1002 itself so as to provide for increased support within the lumbar spine.

Referring still to FIG. 26, the extended outer sleeve 1000 engages the spine laterally, although the surgical approach in reaching the spine may be from an anterior, lateral, or anterior-lateral incision on the outside of the body, and is hereinafter referred to as the "Lateral Method". The "Lateral Method" involves the insertion of a distractor, such as, but not limited to the distractor 100 described above into the lateral aspect of the spine, and generally from a side to side direction although said direction could be slightly from anterolateral to slightly posterolateral (diagonalized from the transverse axis) without departing from the teaching of the method of the present invention to distract the adjacent vertebrae, in this example, $L_4$ and $L_5$. Once the distractor 100 is in place, if fusion alone is to be performed, then the extended outer sleeve 1000 having both anterior and posterior extension members 1020 and 1022 is utilized. The extended outer sleeve 1000 is placed over the distractor 100 such that the posterior extension member 1022 is positioned at the posterior aspect of the spine and the anterior extension member 1020 is positioned at the anterior aspect of the spine. Once the extended outer sleeve 1000 is in place, the distractor 100 is removed. Alternatively, it is appreciated that the "Lateral Method" may be performed without the use of a distractor. Instead, the extended outer sleeve 1000 may be inserted from the lateral aspect of the spine directly since the extension members 1020 and 1022 function to distract the adjacent vertebrae $L_4$ and $L_5$ to restore and maintain the normal angular relationship of those vertebrae $L_4$ and $L_5$.

If the implant to be inserted has surface irregularities such that there is a major diameter (including the surface irregularities) and a minor diameter (excluding the surface irregularities), then an inner sleeve 1040 similar to the inner sleeve 242 described above, may be inserted into the extended outer sleeve 1000. The inner sleeve 1040 functions as a drill guide and spacer having a thickness which corresponds to the difference between the major and minor diameters of such implant as described in detail above in reference to an inner sleeve 1040. A drill 250, described above, is inserted into the inner sleeve 1040 and is used to drill the vertebrae with the inner sleeve 1040 providing a more intimate fit to the drill 250, than the larger bore of the extended outer sleeve 1000 could have alone and thus more precisely controlling the path of the drill 250. The inner sleeve 1040 and the drill 250 may be removed from the extended outer sleeve 1000 together thus trapping and removing much of the debris produced by the actual drilling. It is appreciated that in the alternative, a drill (not shown) may be used such that the distal bone engaging portion has an outside diameter generally corresponding to the minor diameter of the implant and more proximally, a shaft portion with a larger diameter generally corresponding to the major diameter of the implant. An implant I may then be inserted according to the method described above. If the implant to be inserted does not have a major and minor diameter, then no inner sleeve is required, and the drill 250 having a diameter corresponding with the diameter of such an implant may be inserted directly into extended outer sleeve to drill the vertebrae $L_4$ and $L_5$.

While not considered the preferred method under most circumstances it is nevertheless anticipated that one could drill the described hole across the disc space and into each of the adjacent vertebrae from the lateral aspect of the spine and in at least a partially side to side direction through the extended outer sleeve and then remove the extended outer sleeve and insert at least one spinal implant also from the lateral aspect of the spine and in an at least a partially side to side direction and with or without the use of some form of spinal distractor. In which circumstance the use of an inner sleeve is of less importance than that the size of the opening created is sufficient such that it is possible to insert the implant. To that end and independent of whether the extended outer sleeve is left in place for implant insertion, and whether an inner sleeve is used during drilling it is anticipated and should be appreciated that the extended outer sleeve and opening may be of a variety of shapes and that the creation of spaces of varied shapes across a disc and within the spine may be achieved by use of an instrument appropriate for the surgical removal of spinal material, such as a chisel or a router, and with or without the use of a drill, and/or an inner sleeve, and/or an extended outer sleeve; and with the essential element being that the space within the spine is being created across a disc intermediate two adjacent vertebrae from the lateral aspect of said disc and at least in part in a from side to side direction and that an implant is then inserted also from the lateral aspect of said disc which implant occupies at least in part said space, engages at least in part each of the vertebrae adjacent said disc space and comes to lie in an at least partially side to side direction across said disc space.

Figure 30A:
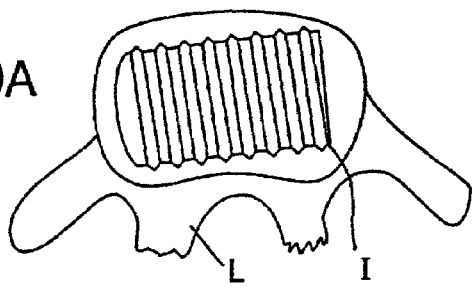
FIG. 30A is a top sectional view similar to FIG. 30 showing the area of contact of a spinal implant inserted from slightly anterior (anterolateral) along the lateral aspect of the spine and oriented at least partially from side to side with respect to the vertebra.
Figure 29:
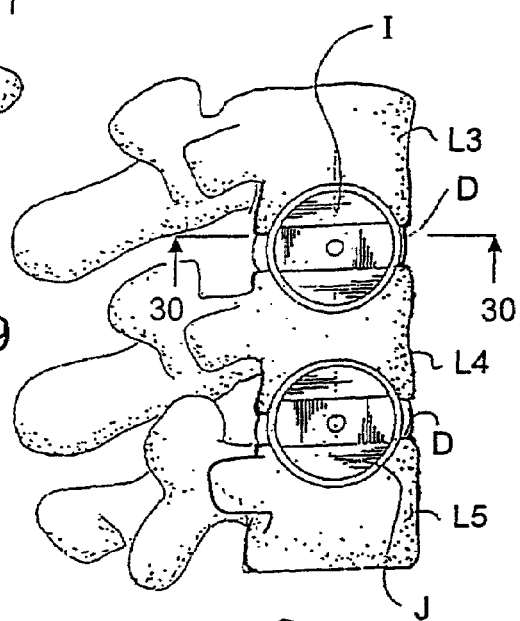
FIG. 29 is a side elevational view of a segment of the lumbar spine with a first spinal implant inserted from the lateral aspect into a hole drilled across a first disc space and into two adjacent vertebrae, and a second spinal implant inserted from the lateral aspect into a second hole drilled across a second disc space and into two adjacent vertebrae.
Figure 30:
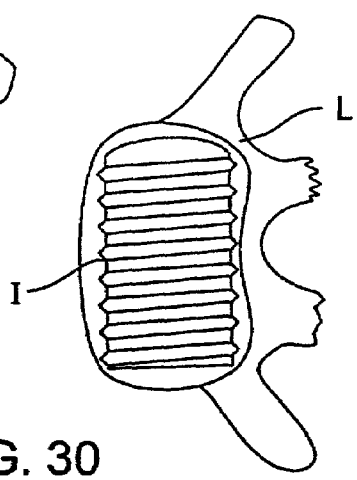
FIG. 30 is top sectional view along lines 30—30 of FIG. 29 showing the area of contact of the first spinal implant and the vertebra.

Referring to FIGS. 29 and 30, the implants I and J are shown inserted across the disc spaces D between vertebrae $L_3$, $L_4$ and $L_5$, respectively. FIG. 30 is a top sectional view along lines 30—30 of FIG. 29 showing the area of contact of the implant I and the vertebrae $L_4$. It can be seen from FIG. 30 that the implant I has a true lateral orientation with respect to the vertebra $L_4$, such that there is a great area of contact between the implant I and the vertebra $L_4$.

Referring to FIG. 30A, a top sectional view of a vertebra similar to FIG. 30 is shown illustrating the area of contact of the implant I and the vertebrae $L_4$ when the implant I is inserted with the "Lateral Method" of the present invention from a slightly anterior position (anterolateral) along the Lateral aspect of the spine and in an at least partially side to side direction.

Figure 31:
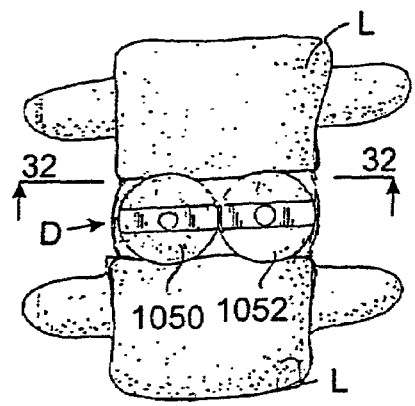
FIG. 31 is an anterior elevational view of a segment of the lumbar spine with spinal cylindrical implants inserted from the anterior of the spine into holes drilled across the same disc space and into two adjacent vertebrae.
Figure 32:
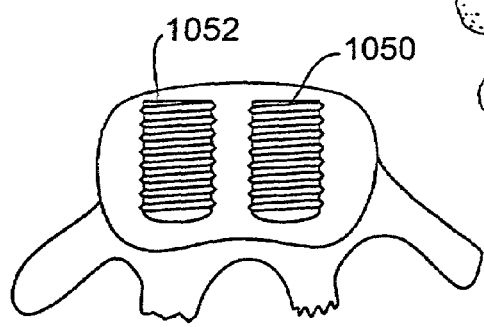
FIG. 32 is a top sectional view along lines 31—31 of FIG. 31 showing the area of contact of the two spinal implants and the vertebra which is the same size as the vertebra of FIG. 30.

Referring to FIGS. 31 and 32, illustrating the prior art method, two implants 1050 and 1052 are inserted from the anterior or posterior aspect of the spine so that they are oriented in an anterior to posterior direction across the disc space D and vertebrae $L_4$ and $L_5$. It can be seen that implants 1050 and 1052 must have a much smaller diameter than implant I to fit within the width of the spine and therefore have very small areas of engagement to the vertebrae themselves as most of the diameter of the implants is used in just spanning across the height of the disc before contacting said vertebrae. FIG. 32 is a top sectional view along lines 32—32 of FIG. 31 showing the area of contact of the two spinal implants 1050 and 1052 and the vertebra $L_5$.

Figure 33:
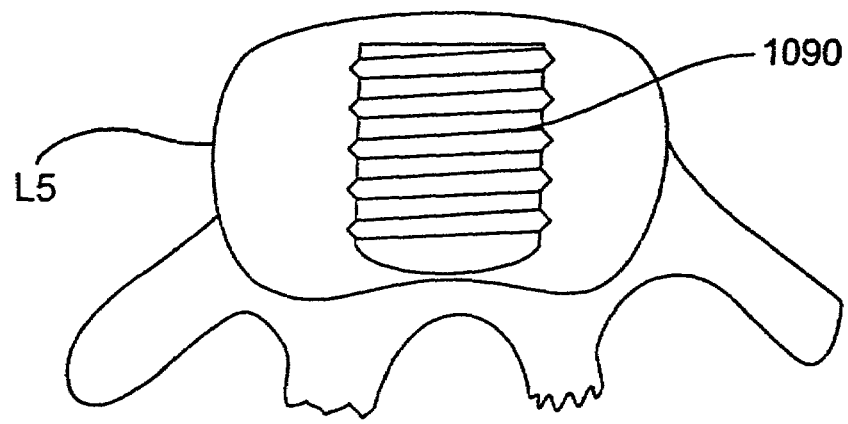
FIG. 33 is a top sectional view of a single implant having a diameter equal to the diameter of the implant of FIG. 30 showing the area of contact with the vertebra which is the same size as the vertebra of FIG. 30.

Referring to FIG. 33, a top sectional view showing the area of contact of a cylindrical spinal implant 1090 having the same diameter as implant I shown in FIG. 30, inserted from the anterior to posterior direction across the vertebra $L_5$ is shown and seen to have by necessity a much shorter length.

Referring to FIGS. 30 and 32–33, it can then be appreciated that an implant I inserted from the lateral aspect of the spine may have a diameter almost as great as the depth of the spine from front to back at that location unlike two implants such as implants 1050 and 1052 inserted side by side from front to back or the reverse where each implant can have a diameter no greater than one half the width of the spine at that level. It can further be appreciated that while the height of the disc space itself hardly affects the area of contact of the single large implant I with the adjacent vertebrae, it substantially effects the area of contact of the two implants 1050 and 1052 inserted in the front to back directions side by side. Further, as the lumbar vertebrae and discs are much wider from side to side then they are deep from front to back, it can be appreciated that when single implants of the same diameter are inserted across a given lumbar disc, the laterally inserted implant I may be of a much greater length and thus have more area of contact, for stability and fusion than implant 1090 inserted from anterior to posterior.

Figure 34:
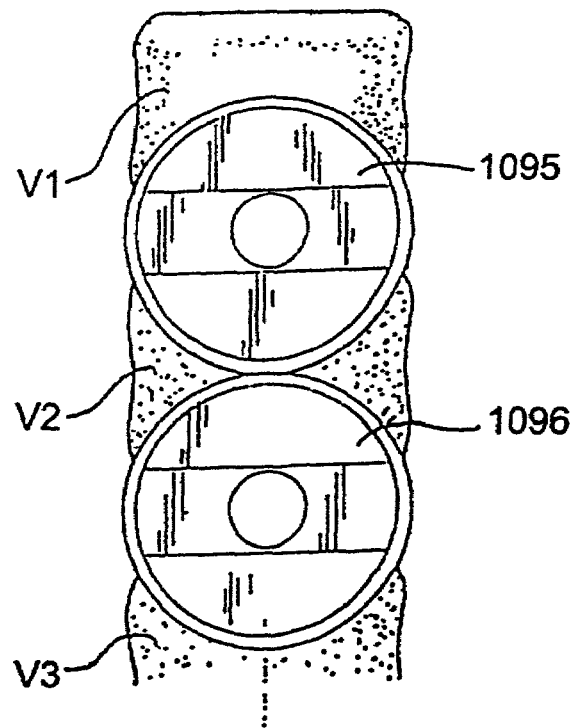
FIG. 34 is a side elevational view of a segment of the spinal column with two spinal implants inserted from front to back at adjacent disc levels between three vertebrae.

Referring to FIG. 34, a segment of the spinal column having single implants 1095 and 1096 inserted from front to back at adjacent disc levels between three vertebrae $V_{1-3}$ is shown. As it can be seen in FIG. 34, it is generally not possible to increase the diameter of singular implants inserted from front to back without risking severe structural and vascular damage to that area of the spine. Implants 1095 and 1096 each have a diameter that is substantially greater than the diameter of implant 1090, such that implants 1095 and 1096 could in theory have a greater area of contact with the adjacent vertebrae than implant 1090. However, in application, as a result of the larger diameter of the implants 1095 and 1096, a large portion of bone from the adjacent vertebrae would have to be removed to accommodate the large diameter of each of the implants 1095 and 1096 which would significantly weaken the structural integrity of those vertebrae. This is especially a problem when as shown in FIG. 34, implants 1095 and 1096 are inserted at adjacent disc levels such that the intermediate vertebrae $V_2$ would be cut in half to form a "butterfly" pattern resulting in the complete loss of the structural integrity of vertebrae $V_2$.

Thus, the implant I of the present invention inserted laterally provides for greater surface area of contact, the largest volume of fusion promoting material, and the greatest mechanical engagement and thus stability, and is therefore an improvement upon other methods of implant insertion in facilitating a successful fusion.

Referring to FIG. 35, an alternative embodiment of the extended outer sleeve is shown and generally referred to by the numeral 1100. As only a single relatively small incision (approximately three inches or less) is required through the abdominal wall of the patient to perform the procedure for the fusion of two vertebrae adjacent a disc space in the lumbar spine, it is anticipated that the surgeon may prefer to perform the method of the present invention under direct vision, without the need for an endoscope. In such a circumstance, a convertible extended outer sleeve 1100 may be used. The convertible extended outer sleeve 1100 may be similar in structure to the extended outer sleeve 1000, except that it comprises a hollow tubular member 1102 that is disengageable from the distal end portion 1104 of the convertible extended outer sleeve 1100. As shown in FIG. 35 the extended outer sleeve 1100 has a detachable hollow tubular member 1102. The vertebrae engaging distal end portion 1104 may be as shown in FIG. 35 or may be similar to the distal end shown previously in FIG. 7A, such that the convertible extended outer sleeve 1100 may be useable throughout the spine.

The convertible extended outer sleeve 1100 is inserted in the disc space D and the adjacent vertebrae $L_4$ and $L_5$ as described above for the extended outer sleeve 1000. Once the extension member 1120 is seated in the disc space D and the prongs 1112 and 1114 are engaged to the vertebrae $L_4$ and $L_5$, the hollow tubular member 1102 may be dissociated from the distal end portion 1104 which remains engaged to the vertebrae $L_4$ and $L_5$. In this manner, if an incision is made to access the spine directly, the surgeon may access the disc space D through the distal end portion 1104 which is closer to the spine, without having to pass through the entire length of the convertible extended outer sleeve 1100. With the distal end portion 1104 in place, the vertebrae remain distracted and aligned, and since the hollow tubular member 1102 has been removed, it is then possible for the surgeon to work in and around the spine under direct vision. The shortened distal end portion 1104 of the convertible extended outer sleeve 1100 left protruding from the adjacent vertebrae may be selected to be of a length such that it still serves to offer some protection to the large blood vessels which are safely positioned outside of the remaining working channel. Alternatively it can be of any length so as to fulfill the surgeon's purposes. The hollow tubular member 1102 may be re-engaged to the distal end portion 1104 for inserting an implant I in the manner described above.

In the specific embodiment of the convertible extended outer sleeve 1100, the distal end portion 1104 has a single extension member 1120 and two prongs 1112 and 1114 positioned approximately 120 degrees from the extension member 1120 for engaging the two adjacent vertebrae $L_4$ and L$_5$, for the purpose of allowing the surgeon direct access to the spinal canal. Thus, if a discectomy is to be performed, an extended outer sleeve having a single anterior intradiscal extended member 1120, but without a posterior extended member, and with two vertebrae engaging prongs 1112 and 1114 may be used.

It is appreciated that for surgery on the thoracic spine, while the method described above wherein the entire procedure is performed through the extended outer sleeve 140 is preferred, it is also possible to utilize the convertible extended outer sleeve 1100 when a full thoracotomy is made to access the thoracic spine without having to work through the entire length of the extended outer sleeve. In this manner the surgeon may directly visualize and access the surgical site.

Further, combining the features of the absence of any posterior intradiscal extended member with the convertible extended outer sleeve 1100 permits easy and direct access to the spinal canal for removal of any diseased discal material.

While the present invention has been described in detail with regards to the preferred embodiments, it is appreciated that other variations of the present invention may be devised which do not depart from the inventive concept of the present invention.

What is claimed is:

1. A method for performing surgery on a spinal segment including a disc space and two vertebral bodies adjacent the disc space, the method comprising the steps of:

positioning one end of a hollow guard in contact with the adjacent vertebral bodies, said guard having at least one projection extending distally from a distal end of said guard, said distal end adapted to contact each of the vertebral bodies adjacent the disc space to be fused, said at least one projection adapted to penetrate the disc space so as to be located at least in part between the perimeters of the vertebral bodies where adjacent to the disc space, said at least one projection having opposed portions adapted to contact at least a portion of each of the adjacent vertebral bodies, respectively, from within the disc space;

removing, through said guard, bone from the adjacent vertebral bodies to form an opening across the surgically corrected height of the disc space and into a portion of each of the two adjacent vertebral bodies;

inserting, through said guard and into the opening, an implant having opposed surfaces each adapted to contact one each of the adjacent vertebral bodies, each of said opposed surfaces having at least one opening to permit for the growth of bone from adjacent vertebral body to adjacent vertebral body through said implant; and utilizing an endoscope to visualize the position of at least a portion of at least one of said implant and said guard relative to the vertebral bodies.

2. The method of claim 1, wherein the utilizing step includes utilizing an endoscope that is a thorascope.

3. The method of claim 1, wherein the positioning step includes the step of engaging said one end of said guard to the two adjacent vertebral bodies.

4. The method of claim 1, wherein the positioning step includes the substep of positioning said guard having at least a second projection extending distally from the distal end of said guard, said at least second projection adapted to penetrate the disc space so as to be located at least in part between the perimeters of the vertebral bodies where adjacent the disc space, said at least second projection having opposed portions adapted to contact at least a portion of each of the adjacent vertebral bodies, respectively, from within the disc space.

5. The method of claim 1, wherein said projection is at least in part co-linear with an outer perimeter of said guard.

6. The method of claim 1, wherein said projection is a tooth.

7. The method of claim 1, wherein the positioning step includes the substep of positioning said guard that is a tubular sleeve.

8. The method of claim 1, further comprising the step of using a distractor to position the adjacent vertebral bodies relative to one another.

9. The method of claim 8, wherein the utilizing step includes visualizing the position of at least a portion of said distractor with said endoscope relative to the vertebral bodies.

10. The method of claim 1, wherein the removing step includes the use of a bone removal device to form the opening and the utilizing step includes visualizing the position of at least a portion of said bone removal device with said endoscope relative to the vertebral bodies.

11. The method of claim 1, wherein the removing step includes the substep of one of milling and drilling the opening.

12. The method of claim 1, further comprising the step of tapping the opening through said guard and the utilizing step includes visualizing the position of at least a portion of said tap with said endoscope relative to the vertebral bodies.

13. The method of claim 1, wherein the inserting step includes the substep of screwing said implant into the opening through said guard.

14. The method of claim 1, wherein the inserting step includes using an insertion instrument to insert said implant into the opening and the utilizing step includes visualizing the position of at least a portion of said insertion instrument with said endoscope relative to the vertebral bodies.

15. The method of claim 1, wherein the inserting step includes inserting said implant comprising a fusion-promoting substance.

16. The method of claim 1, wherein said implant includes at least in part one of bone, coral, and artificial material.

17. The method of claim 1, wherein said implant is in the shape of one of a cylinder, a partial cylinder, and a dowel.

18. The method of claim 1, further comprising the step of combining said implant with a fusion promoting substance.

19. The method of claim 18, wherein the fusion promoting substance includes at least one of bone, bone morphogenetic protein, hydroxyapatite, hydroxyapatite tricalcium phosphate, and coral.

20. The method of claim 19, wherein said implant is at least in part hollow, the step of combining including loading said implant with the fusion promoting substance.

21. The method of claim 19, wherein the step of combining includes coating said implant with the fusion promoting substance.

22. The method of claim 1, wherein the method is performed without distracting the adjacent vertebral bodies between the removing step and the inserting step.

23. The method of claim 1, wherein the method is performed without removing the guard between the positioning step and the inserting step.

24. The method of claim 1, wherein the inserting step includes the substep of providing said implant having upper and lower portions having at least one protrusion on said upper and lower portions for engaging the adjacent vertebral bodies.

25. The method of claim 24, wherein said protrusion is at least a portion of a thread.

26. A method for performing surgery on a spinal segment including a disc space and two vertebral bodies adjacent the disc space, the method comprising the steps of:
positioning one end of a hollow guard in contact with the adjacent vertebral bodies said guard having at least one projection extending distally from a distal end of said guard, said distal end adapted to contact each of the vertebral bodies adjacent the disc space to be fused, said at least one projection adapted to penetrate the disc space so as to be located at least in part between the perimeters of the vertebral bodies where adjacent to the disc space, said at least one projection having opposed portions adapted to contact at least a portion of each of the adjacent vertebral bodies, respectively, from within the disc space;
removing, through said guard, bone from the adjacent vertebral bodies to form an opening across the disc space and into a portion of each of the two adjacent vertebral bodies;
inserting, through said guard and into the opening, an implant having rigid opposed surfaces each adapted to contact one each of the adjacent vertebral bodies; and
utilizing an endoscope to visualize the position of at least a portion of at least one of said implant and said guard relative to the vertebral bodies.

27. The method of claim 26, wherein the utilizing step includes utilizing an endoscope that is a thorascope.

28. The method of claim 26, wherein the positioning step includes the step of engaging said one end of said guard to the two adjacent vertebral bodies.

29. The method of claim 26, wherein the positioning step includes the substep of positioning said guard having at least a second projection extending distally from the distal end of said guard, said at least second projection adapted to penetrate the disc space so as to be located at least in part between the perimeters the vertebral bodies where adjacent the disc space, said at least second projection having opposed portions adapted to contact at least a portion of each of the adjacent vertebral bodies, respectively, from within the disc space.

30. The method of claim 26, wherein said projection is at least in part co-linear with an outer perimeter of said guard.

31. The method of claim 26, wherein said projection is a tooth.

32. The method of claim 26, wherein the positioning step includes the substep of positioning said guard that is a tubular sleeve.

33. The method of claim 26, further comprising the step of using a distractor to position the adjacent vertebral bodies relative to one another.

34. The method of claim 33, wherein the utilizing step includes visualizing the position of at least a portion of said distractor with said endoscope relative to the vertebral bodies.

35. The method of claim 26, wherein the removing step includes the use of a bone removal device to form the opening and the utilizing step includes visualizing the position of at least a portion of said bone removal device with said endoscope relative to the vertebral bodies.

36. The method of claim 26, wherein the removing step includes the substep of one of milling and drilling the opening.

37. The method of claim 26, further comprising the step of tapping the opening through said guard and the utilizing step includes visualizing the position of at least a portion of said tap with said endoscope relative to the vertebral bodies.

38. The method of claim 26, wherein the inserting step includes the substep of screwing said implant into the opening through said guard.

39. The method of claim 26, wherein the inserting step includes using an insertion instrument to insert said implant into the opening and the utilizing step includes visualizing the position of at least a portion of said insertion instrument with said endoscope relative to the vertebral bodies.

40. The method of claim 26, wherein the inserting step includes inserting said implant comprising a fusion-promoting substance.

41. The method of claim 26, wherein said implant includes at least in part one of bone, coral, and artificial material.

42. The method of claim 26, wherein said implant is in the shape of one of a cylinder, a partial cylinder, and a dowel.

43. The method of claim 1, further comprising the step of combining said implant with a fusion promoting substance.

44. The method of claim 43, wherein the fusion promoting substance includes at least one of bone, bone morphogenetic protein, hydroxyapatite, hydroxyapatite tricalcium phosphate, and coral.

45. The method of claim 43, wherein said implant is at least in part hollow, the step of combining including loading said implant with the fusion promoting substance.

46. The method of claim 43, wherein the step of combining includes coating said implant with the fusion promoting substance.

47. The method of claim 26, wherein the method is performed without distracting the adjacent vertebral bodies between the removing step and the inserting step.

48. The method of claim 26, wherein the method is performed without removing the guard between the positioning step and the inserting step.

49. The method of claim 26, wherein the inserting step includes the substep of providing said implant having upper and lower portions having at least one protrusion on said upper and lower portions for engaging the adjacent vertebral bodies.

* * * * *

UNITED STATES PATENT AND TRADEMARK OFFICE
CERTIFICATE OF CORRECTION

PATENT NO. : 7,207,991 B2
APPLICATION NO. : 10/100701
DATED : April 24, 2007
INVENTOR(S) : Gary Karlin Michelson It is certified that error appears in the above-identified patent and that said Letters Patent is hereby corrected as shown below:

Title Page 1, Column 1:
Related U.S. Application Data, line 4: change "5,772,661, which is a
 continuation-in-part of appli-" to -- 5,772,661. --; and
Related U.S. Application Data, lines 5-11: delete in their entirety.

Title Page 2, Column 1:
U.S. Patent Documents, line 6: change "Mylier" to -- Myller --; and
U.S. Patent Documents, Insert -- 3,867,932 A 2/1975 Huene --.

Title Page 2, Column 2:
U.S. Patent Documents, Insert -- 4,723,540 A 2/1988 Gilmer, Jr. --.
U.S. Patent Documents, line 59: delete "4,232,679 A 5/1988 Schulman"

Title Page 3, Column 1:
U.S. Patent Documents, Insert -- 5,131,382 A 7/1992 Meyer --; and
U.S. Patent Documents, line 73: delete "4,971,740 A 1/1997 Nishio et al."

Title Page 4, Column 1:
Line 1: change "Encephalomenigoceles" to -- Encephalomeningoceles --; and
Line 12: change "knochemen" to -- knochernen --.

Signed and Sealed this

Twentieth Day of May, 2008

JON W. DUDAS
*Director of the United States Patent and Trademark Office*